US007100839B2

(12) United States Patent
Farina et al.

(10) Patent No.: US 7,100,839 B2
(45) Date of Patent: Sep. 5, 2006

(54) METHOD OF SERVICING COMPANIES ASSOCIATED WITH A SPRAY DEVICE OPERATING UNDER GUIDELINES OF A REGULATORY BODY

(75) Inventors: Dino J. Farina, Holliston, MA (US); Donald C. Swavely, Norton, MA (US); John A. Vennari, New London, CT (US); Leticia M. Broome, Wayland, MA (US); Franklin A. Bales, Leland, NC (US)

(73) Assignee: Image Therm Engineering, Inc., Sudbury, MA (US)

( * ) Notice: Subject to any disclaimer, the term of this patent is extended or adjusted under 35 U.S.C. 154(b) by 99 days.

(21) Appl. No.: 10/824,778

(22) Filed: Apr. 14, 2004 (Under 37 CFR 1.47)

(65) Prior Publication Data

US 2005/0077369 A1 Apr. 14, 2005

Related U.S. Application Data

(60) Provisional application No. 60/462,861, filed on Apr. 14, 2003.

(51) Int. Cl.
*A01G 27/00* (2006.01)

(52) U.S. Cl. ........................ 239/69; 239/380; 239/381; 239/36; 239/68; 239/67; 700/283; 700/282; 73/1.05; 73/865.9; 73/1.02; 73/1.37; 73/1.41

(58) Field of Classification Search ............ 239/67–69, 239/381, 382; 700/283, 282; 73/1.05, 1.02, 73/1.37, 1.41
See application file for complete search history.

(56) References Cited

U.S. PATENT DOCUMENTS 4,357,670 A * 11/1982 McFarlane .................. 700/283
4,415,265 A 11/1983 Campillo et al.
4,614,300 A * 9/1986 Falcoff ......................... 239/71
4,965,841 A 10/1990 Kaneko et al.
4,992,952 A * 2/1991 Sasaki ........................ 700/283

(Continued)

FOREIGN PATENT DOCUMENTS

WO WO 03/000429 A2 1/2003

OTHER PUBLICATIONS

Dvorak, P., "How to See Aerosol Spray Patterns and Plumes," *Machine Design*, 72(13): 122 (Jul. 6, 2000).

(Continued)

*Primary Examiner*—David A. Scherbel
*Assistant Examiner*—James S. Hogan
(74) *Attorney, Agent, or Firm*—Hamilton, Brook, Smith & Reynolds, P.C.

(57) ABSTRACT

A method for servicing companies associated with a spray device operating under guidelines of a regulatory body includes capturing in vitro actuation data associated with operation of the spray device and distributing the data to a company associated with an aspect of the spray device. The company may use the data for testing the spray device to ensure continued compliance with prior approval of the spray device by the regulatory body. The method may also include converting the data to parameters and distributing the parameters. Capturing the in vitro actuation data may include sorting the data based on in vitro age groups. Distributing the data may include providing the data in a format executable by an automated actuation system. The company receiving the data may be a drug development company, spray device manufacturer, or testing service. The regulatory body may be the Food and Drug Administration (FDA).

15 Claims, 18 Drawing Sheets

U.S. PATENT DOCUMENTS

| | | | | |
|---|---|---|---|---|
| 5,075,014 | A | | 12/1991 | Sullivan |
| 5,337,926 | A | | 8/1994 | Drobish et al. |
| RE34,910 | E | | 4/1995 | Funkenbusch et al. |
| 5,561,527 | A | | 10/1996 | Krone-Schmidt et al. |
| 5,879,713 | A | | 3/1999 | Roth et al. |
| 6,149,071 | A | * | 11/2000 | MacCallumMhor et al. .. 239/67 |
| 6,193,936 | B1 | | 2/2001 | Gardner et al. |
| 6,256,597 | B1 | | 7/2001 | Wang et al. |
| 6,508,112 | B1 | | 1/2003 | Verhoeven |
| 6,799,090 | B1 | * | 9/2004 | Farina et al. ............... 700/283 |
| 2005/0001054 | A1 | | 1/2005 | Farina et al. |

OTHER PUBLICATIONS

Badreldin, Amira M., "Real-Time Analysis of Fuel Spray Images," *IEEE*, pp. 622-624 (1987).

Lopera, J. F. G., et al., "Improved Entropic Edge-Detection." Paper supported by grant MAR97-0464-C04-02 of Spanish Government. No date given.

Pastor, J. V., et al., "Analysis Methodology of Diesel Spray and Flame by Means of In-Cylinder Endoscopic Imaging, " (The Institution of Electrical Engineers). Savoy Place, London: IEE (2000).

Sellens, Rick and Deljouravesh, Rama, "Non-Orthogonal Optical Spray Pattern Analysis, " Ninth International Symposium on Applications of Laser Techniques to Fluid Mechanics, Lisbon, Portugal, Jul. 1998.

Sankar, S. V., et al., "Time-Resolved Measurement of Liquid Mass Distribution in a Fuel Injector Spray Using an Optical Patternator," *Institute for Liquid Atomization and Spray Systems, ILASS Americas* '97, pp. 266-270, Ottawa, ON, Canada, May 18-21, 1997.

Wang, G., et al., "An Optical Spray Pattern Analyzer," *Institute for Liquid Atomization and Spray Systems, ILASS Americas*'97, pp. 261-265, Ottawa, ON, Canada, May 18-21, 1997.

"Image Therm Engineering Ships the First SprayVIEW Nsx System," http://www.imagetherm.com/News Releases.asp. 2001.

* cited by examiner (SIDE VIEW)

(SIDE VIEW)

SIDE VIEW

METHOD OF SERVICING COMPANIES ASSOCIATED WITH A SPRAY DEVICE OPERATING UNDER GUIDELINES OF A REGULATORY BODY

RELATED APPLICATION(S)

This application claims the benefit of U.S. Provisional Application No. 60/462,861, filed on Apr. 14, 2003. The entire teachings of the above application are incorporated herein by reference.

BACKGROUND OF THE INVENTION

A spray pump's performance is characterized in terms of its emitted spray pattern, plume geometry, and/or droplet size distribution. These parameters are known to be affected by the means in which the spray pump is actuated. For example, slow actuation will likely cause poor atomization, producing a stream-like flow. Fast actuation will likely produce too fine a spray, leading to poor absorption in the nasal mucosa and unwanted inhalation and deposition of the droplets in the throat and lungs. These factors and others, such as drug compatibility with the spray device, may result in the drug delivery falling outside the criteria associated with an original clinical trial approval. Testing the delivery or spray devices may be done to verify the spray device actuates the drug within the criteria of the original clinical trial approval, but operator actuation variability may adversely affect test results.

SUMMARY OF THE INVENTION

Automated actuation of nasal spray devices subject to in vitro bioequivalence testing may be employed to decrease variability in drug delivery due to operator factors (including removal of potential analyst bias in actuation) and increase the sensitivity for detecting potential differences among drug products. An automated actuation system may include settings for force, velocity, acceleration, length of stroke, and other relevant parameters. Selection of appropriate settings is relevant to proper usage of the product by a trained patient, and, for nasal sprays, may be available from pump suppliers for tests such as droplet size distribution by laser diffraction or spray pattern photographic techniques. In the absence of recommendations from the pump supplier, settings may be documented based on exploratory studies in which the relevant parameters are varied to simulate in vitro performance upon hand actuation. Exploratory studies of hand actuation of the spray pump device are useful to determine appropriate settings for automated actuation.

Accordingly, one embodiment of the principles of the present invention includes an assembly that provides information about operation of a spray device. The assembly includes an adapter assembly configured to be coupled to a movable part of the spray device. In the case of a nasal spray, the movable part is the nasal tip and, in the case of a Metered Dose Inhaler (MDI), the movable part is the canister containing the drug. The assembly also includes a mounting assembly configured to be coupled to a stationary part of the spray device. In the case of the nasal spray device, the stationary part is the bottle containing the drug and, in the case of the MDI, the stationary part is the mouthpiece. The assembly also includes a transducer, coupled to the mounting assembly or the adapter assembly. The assembly also includes a linkage that is adapted to extend between the mounting assembly and the adapter assembly. The linkage is in operational relationship with the transducer to enable the transducer to indicate a mechanical relationship between the movable and stationary parts of the spray device corresponding to the operation of the spray device.

The mounting assembly may include a bearing and shaft assembly coupling the adapter assembly to the mounting assembly. The bearing and shaft assembly may substantially maintain alignment between the adapter assembly and the mounting assembly in non-actuation axes.

The assembly may also include a base assembly adapted to be coupled to the mounting assembly. The base assembly may include a foot assembly with a footprint that supports the spray device in a vertical relationship with the foot assembly. The assembly and spray device may have a predetermined weight for use on a weight measuring scale sensitive enough to measure a change in fluid ejected by the spray device in a single discharge. In one embodiment, the total weight of the assembly and spray device is less than or equal to 200 grams.

The transducer may be a position sensor. An example of one such position sensor is a potentiometer. In the case of the potentiometer, the linkage is a spring loaded wire integrally associated with the potentiometer.

The adapter assembly may be configured to interface with an automated actuation system that operates the spray device in an automated manner. The transducer may indicate the mechanical relationship in a format usable by the automated actuation system.

The assembly may also include a data processing system coupled to the transducer that captures indications of the mechanical relationship between the movable part and the stationary part of the spray device. The data processing system may include program instructions that automatically calculate parameters in position, velocity, or acceleration corresponding to operation of the spray device. The instructions may include a routine that calculates velocity or acceleration data from position measurements using a least squares technique. The parameters may include at least one of the following: maximum position displacement, hold time, maximum actuation velocity, maximum return velocity, maximum actuation acceleration, and maximum return acceleration. The actuation direction is defined herein as the direction in which the movable part causes atomization of the liquid drug contained in the spray device, and the return direction is defined herein as the direction in which the movable part returns to its state of rest. The data processing system may also include a signal conditioner, data sampler, and amplifier, wherein the signal conditioner conditions a signal effected by the transducer prior to the data sampler and amplifier operating on the signal.

The principles of the present invention include corresponding methods related to the above-described apparatus and alternative embodiments thereof described below.

Another embodiment according to the principles of the present invention includes a method for servicing companies associated with a spray device operating under guidelines of a regulatory body. The method includes capturing in vitro actuation data associated with operation of the spray device. The method also includes distributing the data to a company associated with an aspect of the spray device. The company may use the data for testing the spray device to ensure continued compliance with prior approval of the spray device by a regulatory body.

The method may also include converting the data to parameters and distributing the data in the form of the parameters. The spray device may include a stationary part and a movable part, and the data may represent a mechanical relationship between the stationary part and the movable part versus time. The method may also include measuring position, velocity, or acceleration relationships between the stationary part and the movable part.

Capturing the in vitro actuation data may include sorting the data based on in vitro age groups. Capturing the in vitro actuation data may also include determining a minimum number of priming strokes by hand actuation. Further, capturing the in vitro actuation data may include determining actuation parameter ranges by hand actuation. Capturing the in vitro actuation data may include determining an initial estimation of delivery performance congruency between hand and automated actuation. The method may also include adjusting automated actuation parameters associated with the automated actuation to achieve a desired shot weight and to determine acceptable ranges.

Distributing the data may include providing the data in a format executable by a machine configured to actuate the spray device in an automated manner. Prior approval may be a clinical trial approval.

The company receiving the data may be a drug development company, spray device manufacturer, or testing service. The regulatory body may be the Food and Drug Administration (FDA).

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
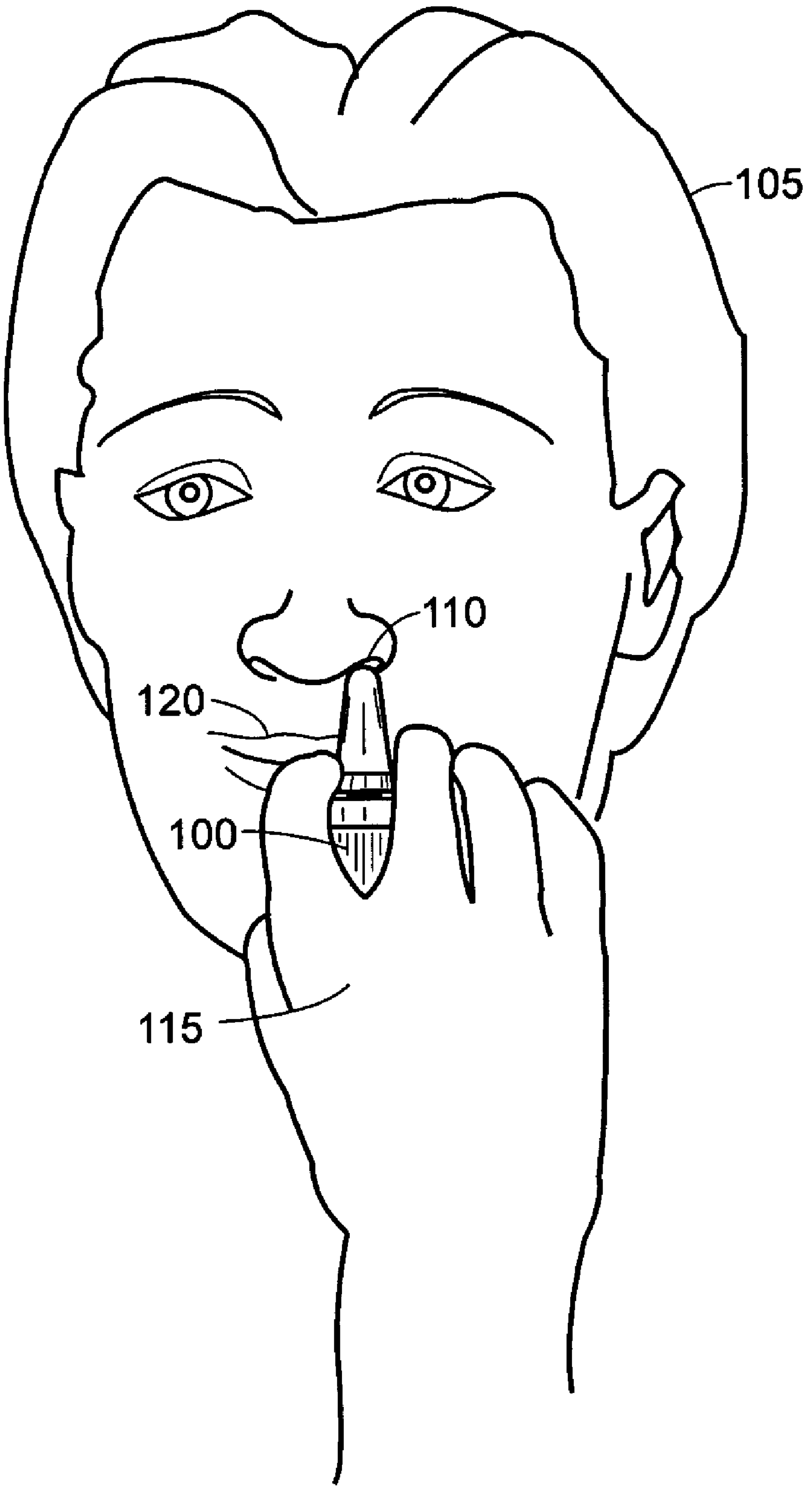
FIG. 1 is an illustration of an example application in which the principles of the present invention may be employed.

FIG. 1 illustrates a spray device application in which the principles of the present invention may be employed. A person 105 uses a spray device 100, such as a nasal spray pump or Metered-Dose Inhaler (MDI), to receive a drug supplied in a liquid form. In the case of a nasal spray pump, the person 105 uses his hand 115 to actuate the spray device 100 to cause the liquid drug to be atomized and projected into a nostril 110. In the case of an MDI, the person 105 uses hand actuation to project an atomized drug into his mouth 120.

It has been observed that different age groups apply different forces to the spray devices 100. Therefore, a drug development company and/or spray device manufacturer cannot always predict the amount of drug that will reach the intended nasal mucosa. A regulatory body, such as the Food and Drug Administration (FDA), may approve a given drug for a predetermined dose. However, spray device manufacturers rarely, if ever, know what the appropriate settings should be for automated actuation testing. This is primarily due to the fact that the device manufacturers rarely have the requisite knowledge of the physical properties of the drug formulation (e.g., viscosity and surface tension) because the formulations are proprietary to the drug company. Thus, the spray device manufacturers generally do not know how these properties will affect the characteristics of the spray the spray device produces when actuated by hand or by an automated actuation system. Additionally, the spray device manufacturer may not have the same automated actuation system as the drug company, thereby further reducing their ability to supply the appropriate actuation settings to the automated actuation system. Moreover, in practice, based on a person's age group, the amount of drug ejected (i.e., dosage) from the spray device 100 may be different from expected. Therefore, the amount absorbed by the person 105 may be different from what the regulatory body approved in clinical trials, thereby causing concern that a person's response to the drug may be different from the criteria determined to be safe and effective in the clinical trials. Some other factors that affect the amount of drug discharged by the spray device 100 are atomization rate of the drug, droplet size, spray pattern, plume geometry, priming and re-priming rates, and environmental conditions.

Figure 2A:
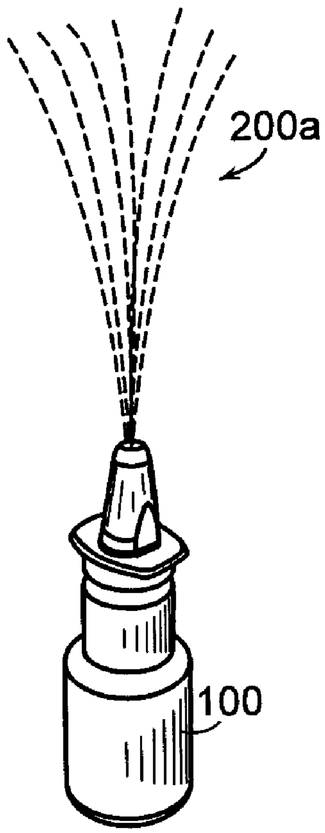
FIGS. 2A–2B are diagrams of spray devices ejecting an atomized drug produced by actuation of the spray device containing the drug used in the application of FIG. 1.
Figure 2B:
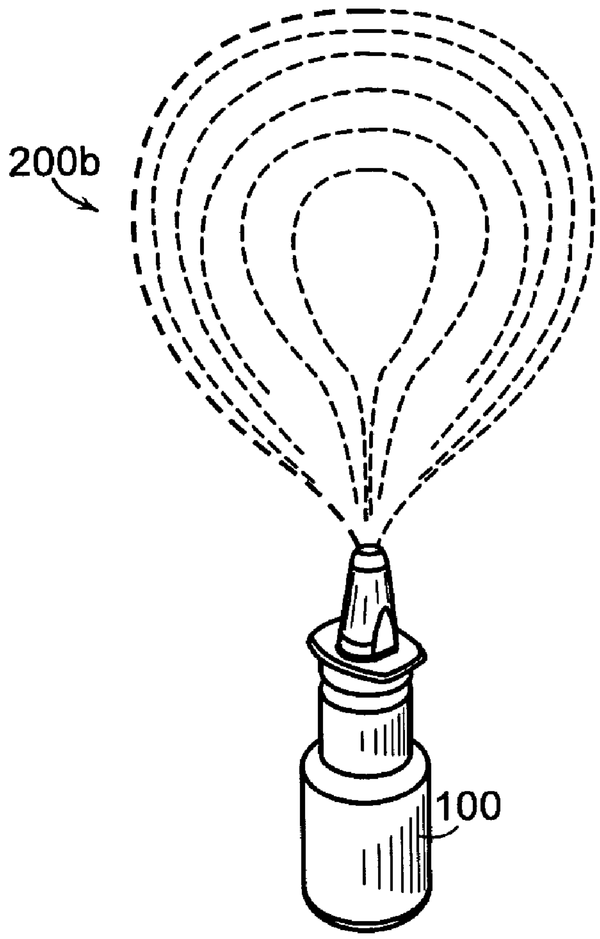

FIGS. 2A and 2B illustrate spray patterns 200*a* and 200*b*, respectively, produced by the same or different spray devices 100. In FIG. 2A, the spray pattern 200*a* is projected in a relatively conical pattern. In FIG. 2B, the drug is more atomized than in FIG. 2A as evidenced by a broader spray pattern 200*b*.

Spray pattern studies characterize a spray either during the spray prior to impaction or following impaction on an appropriate target, such as a thin-layer chromatography (TLC) plate. Spray patterns for certain nasal spray products may be spoked or otherwise irregular in shape.

Spray patterns can be characterized and quantified by either manual or automated image analysis. Both analyses allow shape and size to be determined. Automated analysis systems may also allow determination of Center of Mass (COM) and/or Center of Gravity (COG) within the pattern to be determined.

Plume geometry describes a side view of the aerosol cloud parallel to the axis of the plume. High-speed photography, laser light sheet, and high speed digital camera or other suitable methods are generally used to determine plume geometry.

Priming and re-priming data also ensure delivery of a dosage of drug and are taken into account when measuring spray patterns 200*a* and 200*b* to accurately model in vitro operation.

Figure 3:
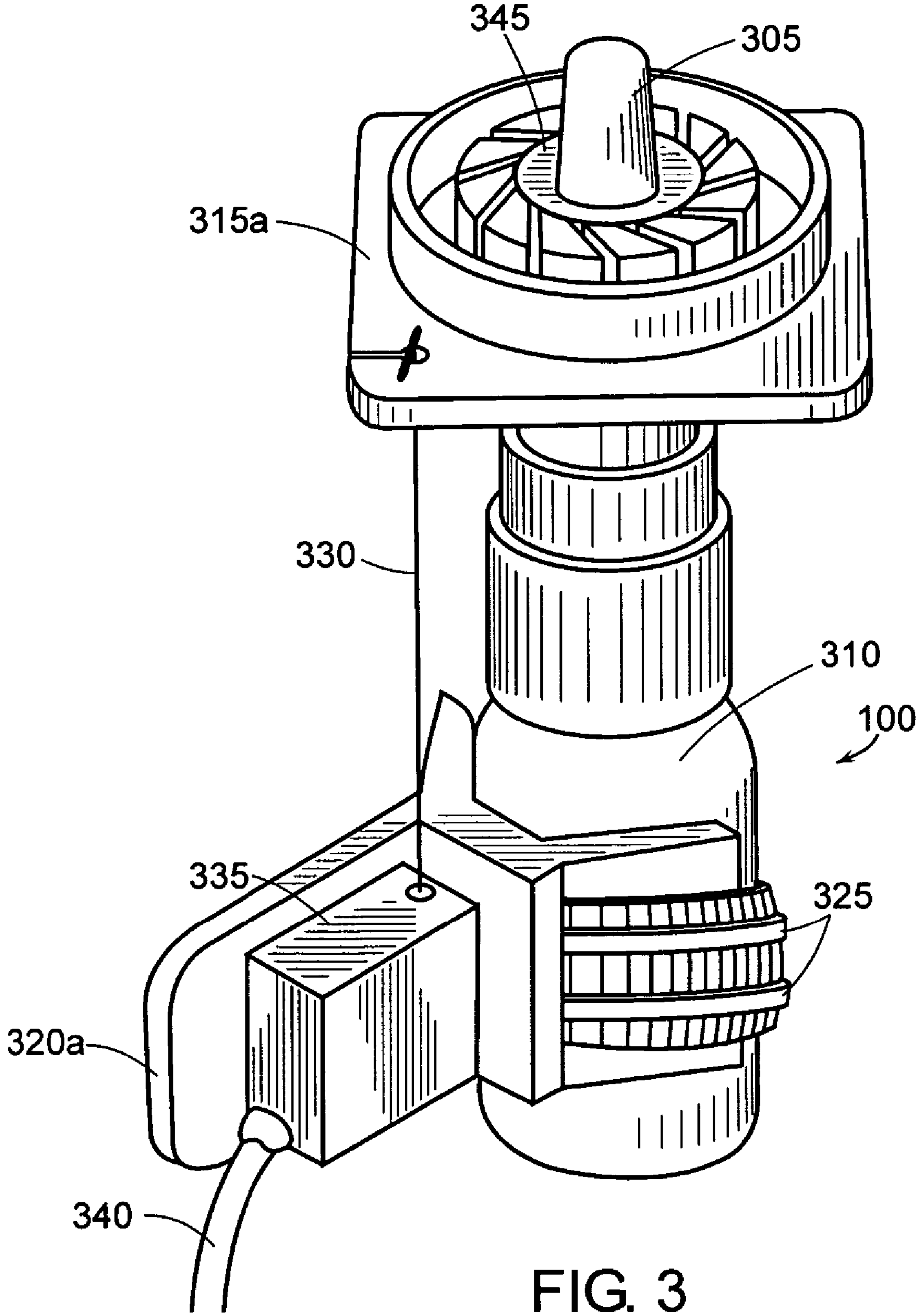
FIG. 3 is a diagram of an assembly connected to the spray device of FIG. 1.

FIG. 3 is an illustration of an example assembly that may be adapted to interface with the spray device 100. In accordance with the principles of the present invention, the assembly is adapted to indicate a mechanical relationship between a movable part 305 and a stationary part of the spray device 100 corresponding to operation of the spray device 100. In a nasal spray pump application, the movable part 305 may be referred to as a nasal tip since it is inserted into the nostril 110. The stationary part 310 may be referred to as a nasal spray pump bottle in this application.

Components that are connected to the spray device 100 include (a) an adapter assembly 315*a*, which connects to the movable part 305, (b) a mounting assembly 320*a*, which connects to the spray device 100, (c) a transducer 335, which is connected to the mounting assembly 320*a* in this embodiment but may be connected to the adapter assembly 315*a* in other embodiments, and (d) a linkage 330, which may be a spring loaded draw wire that is adapted to extend between the mounting assembly 320*a* and adapter assembly 315*a*. The linkage 330 is in operational relationship with the transducer 335 to enable the transducer 335 to indicate the mechanical relationship between the movable part 305 and the stationary part 310 of the spray device 100 corresponding to operation of the spray device 100.

The transducer 335 may be a position sensor, such as a potentiometer. Extending from the potentiometer is a transducer cable 340 providing a transducer output. The transducer cable 340 connects at the other end (not shown) to a data acquisition (DAQ) circuit board (not shown) or other electronics to capture and/or process the transducer output.

The mounting assembly 320*a* may be connected to the stationary part 310 through use of flexible tie straps 325. Other connection means may also be used, such as Velcro® straps, adhesive, or other suitable attachment means. A rubber or other suitable material may be used to form a solid connection between the adapter assembly 315*a* and the movable part 305. Securing of the adapter assembly 315*a* or the mounting assembly 320*a* to the respective parts 305, 310 of the spray device 100 may be completed through screw means, latching mechanism, or other suitable mechanism.

In this particular embodiment, the draw wire 330 is kept taut enough by the spring in the transducer 335 to prevent sluggishness without deflecting the movable part 305 of the spray device 100 or the adapter assembly 315*a*. The lateral location of the transducer 335 relative to the mounting assembly 320*a* is then adjusted and tightened against the mounting assembly 320*a* so that the draw wire 330 is parallel to the actuation axis of the spray device 100.

In operation, a person 105 operates the spray device 100 in a typical manner by placing his fingers on the adapter assembly 315*a* and drawing it toward the mounting assembly 320*a* to cause the movable part 305 to move. The motion produces a "shot" or dosage to the expelled from the spray device 100. When the spray device 100 is actuated, the linkage 330 causes the transducer 335 to change its state. A change in state of the transducer 335 causes the transducer output to change state in a proportional manner. The data acquisition circuit board (not shown) captures the change in state of the transducer 335 and provides the captured data to a processor for further processing. Prior to testing, the transducer 335 may be calibrated and used during the processing.

Figure 4:
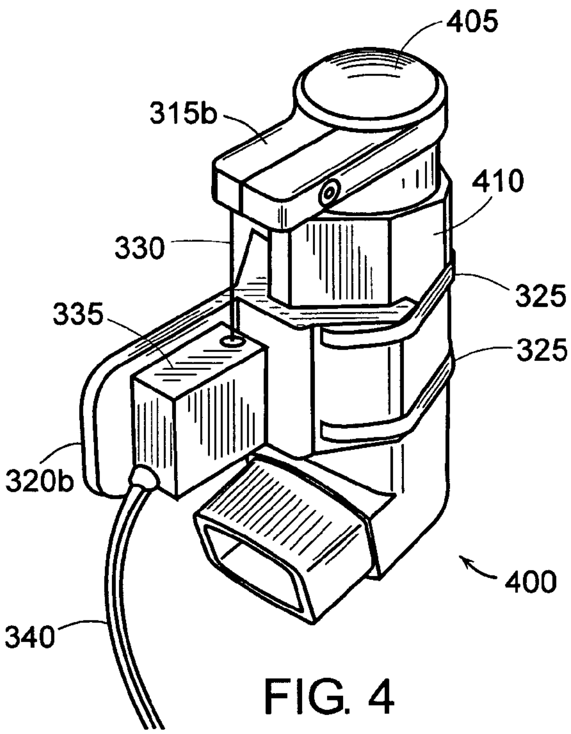
FIG. 4 is an alternative embodiment of the assembly of FIG. 3.

FIG. 4 is an illustration of the components applied to a metered-dose inhaler (MDI) 400. The spray bottle 100 and MDI 400 are interchangeably referred to herein as "spray devices". In the case of the MDI 400, a pressurized canister 405 is the movable part, and a mouthpiece 410 is the stationary part. A person's hand 115 squeezes the pressurized canister 405 toward the mouthpiece 410 to actuate the MDI 400 and cause a "shot" to be expelled from the MDI 400.

Similar to its usage with the spray bottle 100, the linkage 330 extends between the adapter assembly 315*b* and mounting assembly 320*b*. The linkage 330 causes the transducer 335 to change states, which is transmitted by way of the transducer cable 340 to a data acquisition system or other processor (not shown).

Figure 5A:
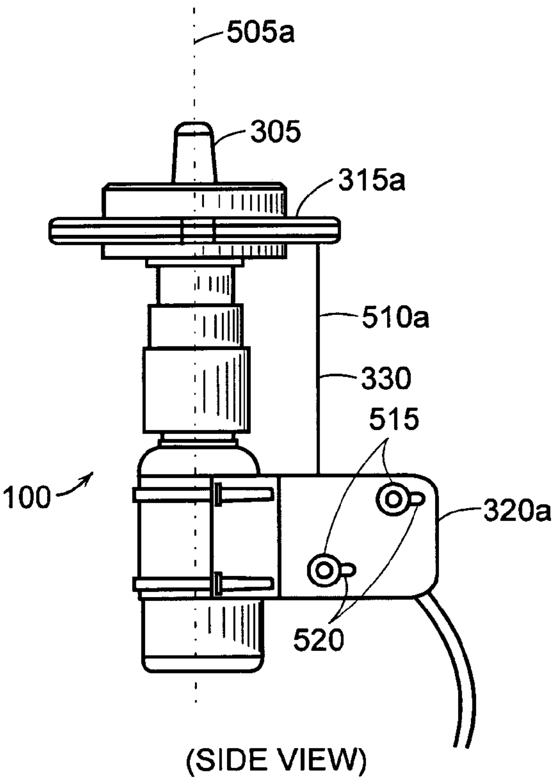
FIGS. 5A–5B are side views of the assembly embodiments of FIGS. 3 and 4, respectively.
Figure 5B:
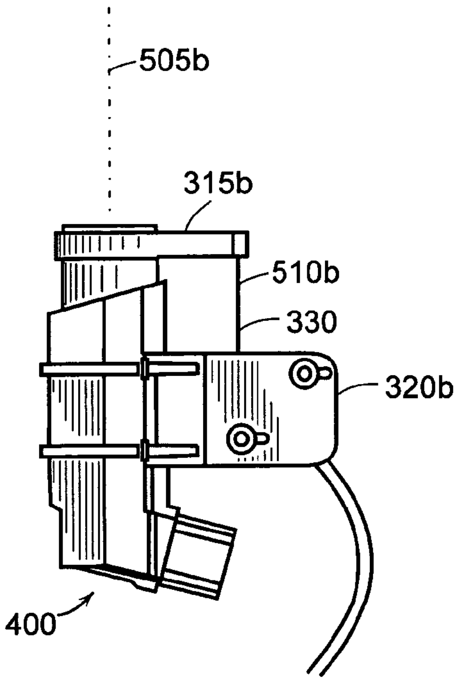

FIGS. 5A and 5B include indications of axes associated with the spray devices 100 and 400. Referring to FIG. 5A, an actuation axis 505*a* extends from the movable part 305, and a draw wire axis 510*a* extends along the linkage 330. Also indicated in FIG. 5A is a pair of adjustment slots 520 and corresponding adjustment screws 515 that hold the transducer 335 (hidden by the mounting assembly 320*a*).

In FIG. 5B, the actuation axis 505*b* extends vertically from the pressurized canister 405, and the draw wire axis 510*b* extends along the linkage 330.

In both cases of spray devices 100, 400, rotation of the linkage 330 about the actuation axis 505*a*, 505*b* causes the transducer 335 to change state much faster than normal operation of the spray device 100 (i.e., actuation along the actuation axis 505*a*, 505*b*). Such a rotation of the linkage 330 is possible if the adapter assembly 315*a*, 315*b* slips (i.e., spins about the actuation axis). Similarly, pivoting of the adapter assemblies 315*a* and 315*b* causes the linkage 330 to rapidly affect the state of the transducer 335. Rapid changes in the output of the transducer 335 affects in vitro measurements. Therefore, the assembly described may be improved by having a more rigid connection between the mounting assembly 320*a* and the adapter assembly 315*a*. An assembly providing a more rigid connection and, therefore, less measurement error, is illustrated in FIG. 6.

Figure 6:
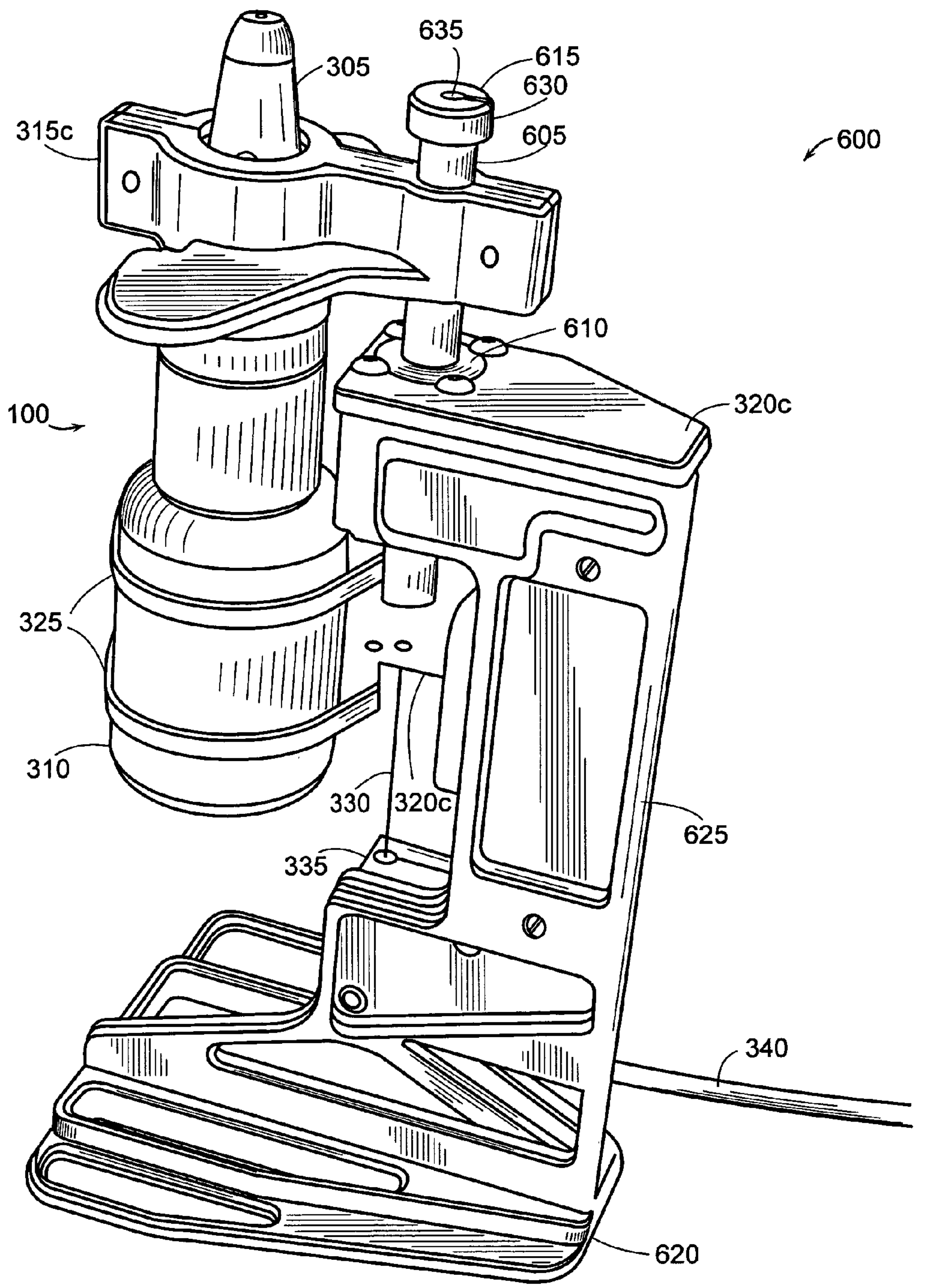
FIG. 6 is an embodiment of the assembly of FIG. 3 in which a shaft and bearing assembly is employed.

FIG. 6 illustrates an embodiment of an assembly 600 that employs a bearing 610 and shaft 605 assembly that substantially maintains alignment between the adapter assembly 315*c* and the mounting assembly 320*c*. The linkage 330 is extended through the shaft 605 and connects to a shaft head 615 by extending through a center hole in the shaft head 615. The linkage 330 may be held in place through use of a slot 630 designed for this purpose.

By using the bearing 610 and shaft 605 assembly, the pivoting of the movable part 305 of the spray device 100 is dramatically reduced over the embodiment of FIG. 3. Further, the assembly 600 may be constructed of lightweight materials, such as aluminum, to allow a person 105 to operate the spray device 100 in an unimpeded manner to simulate typical use of the spray bottle 100. The shaft 605 may be a hardened precision shaft constructed of ¼" O.D. stainless steel. The bearing 610 may be lined with various materials to allow the shaft 605 to travel smoothly and freely, thereby facilitating unimpeded in vitro motion.

In this embodiment, the mounting assembly 320*c* is connected to a foot assembly 620 via a bracket assembly 625. Screws or other connection means are used to connect the bracket assembly 625 to the mounting assembly 320*c* and the foot assembly 620. The foot assembly 620 is adapted to allow the entire assembly 600 to stand in a vertical arrangement such that the spray device 100 is held in a vertical relationship with the foot assembly 620 and suspended above a surface (e.g., weight measuring scale platform or table top) on which the foot assembly 620 rests.

The assembly 600 and spray device 100 may have a predetermined weight for use on a weight measuring scale that is sensitive enough to measure a change in fluid ejected by the spray device in a single discharge. Accordingly, if the foot assembly 620 is frame-like, weight can be minimized to meet a lightweight criterion. For example, the total weight of the assembly 600 and spray device 100 may be required to be less than 200 grams. If even more weight need be removed from the assembly 600, the bracket assembly 625 can also be formed in a frame-like manner, as shown.

Figure 7:
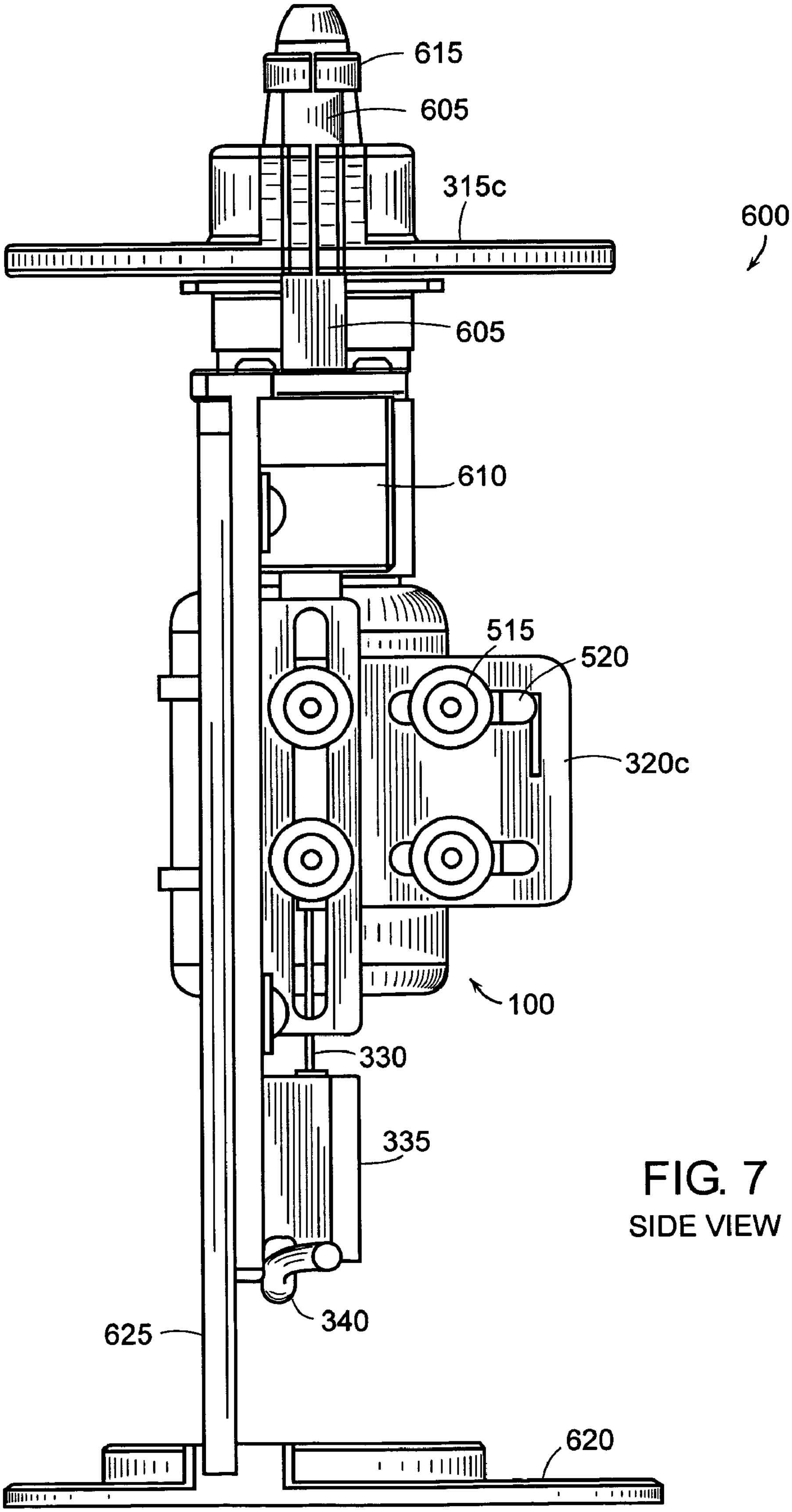
FIG. 7 is a side view of the assembly of FIG. 6.

FIG. 7 is a side view of the assembly 600 with the spray device 100. The mounting assembly 320*c* includes adjustment screws 515 and slots 520 to accommodate spray devices 100 having different diameters. Similar adjustment means may be provided on the adapter assembly 315*c*. Various types of alignment means may be provided to remove motion in a cross-axis to the actuation axis 505*a* (FIG. 5A).

The MDI 400 generally maintains alignment in the actuation axis 505*b*. Therefore, the shaft 605 and bearing 610 design is generally unnecessary for allowing the transducer 335 to indicate the mechanical relationship between the movable part 405 and the stationary part 410 of the MDI 400 without having errors caused by rapid changes in length of the linkage 330.

Figure 8:
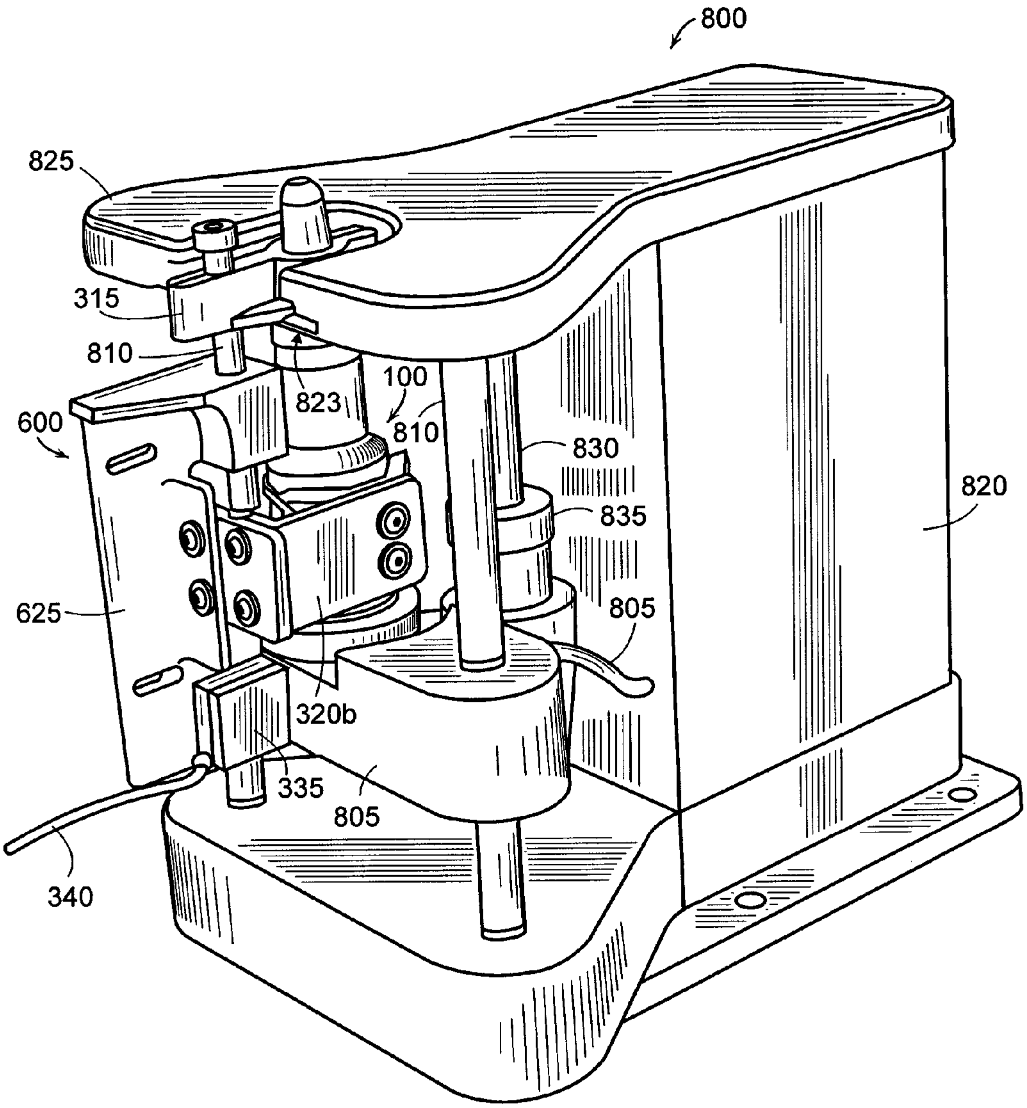
FIG. 8 is a diagram of an automated actuation system used in the application of FIG. 1.

FIG. 8 is an illustration of an automated actuation system 800 that operates the spray device 100 in an automated manner. The automated actuation system 800 includes a compression plate assembly 805 that travels vertically along a pair of passive, parallel, guide bars 810. In one embodiment, a drive motor assembly (not shown) drives a belt and pulley assembly (not shown) that drives a drive plate assembly 835 along a drive rod 830. The drive plate assembly 835 is connected to the compression plate assembly 805 in this embodiment. In response to upward force by the drive plate assembly 835, the compression plate assembly 805 presses upward on the stationary part 310 of the spray device 100 to actuate the spray device 100. Alternatively, a clamp (not shown) or other attachment means may be used to attach the stationary part 310 of the spray device 100 to the compression plate assembly 805. Embodiments of automated actuation systems 800 are further described in co-pending U.S. patent application Ser. No. 10/176,930 entitled, "Precise Position Controlled Actuating Method and System", filed on Jun. 21, 2002; the entire teachings of which are incorporated herein by reference in their entirety.

To facilitate engagement of the assembly 600 with the automated actuation system 800, the adapter assembly 315*c* may be configured to fit into a predefined cut-out 823 in the top 825 of the automated actuation system 800. Also, in this embodiment, the bracket assembly 625 is disconnected from the foot assembly 620 to allow for the proper interfacing of the assembly 600 with the automated actuation system 800.

The motor assembly and a portion of the belt and pulley assembly may be deployed in a housing 820 of the automated actuation system 800. At least one processor (not shown) and voltage or current drive amplifier(s) (not shown) may also be deployed in the housing 820. The drive amplifier(s) may be used to control drive motor(s) in the drive motor assembly.

In one embodiment of the automated actuation system 800, the compression plate assembly 805 includes a force transducer (not shown), such as a piezoelectric transducer, that is positioned to sense actuation force of the spray device 100 caused by upward force applied by the compression plate assembly 805. The force transducer may convert force to an output signal (e.g., voltage, current, or charge) in a proportional manner and transmit the output signal on a cable 815 to a sense amplifier (not shown). The sense amplifier is adapted to receive the output signal and convert it to a signal, with minimal additional noise, that can be sampled and processed by the processor.

Alternative embodiments of the automated actuation system 800 may also be employed. For example, the compression plate assembly 805 may include the drive motor assembly, which may employ linear voice coil motor(s), and the drive amplifier(s) may be in the housing 820. In such an embodiment, the cable 815 carries electrical power signals between the drive amplifier(s) and motor(s) (not shown) in the compression plate assembly 805. The cable 815 may also include feedback wires to allow for closed-loop control. Alternatively, the compression plate assembly 805 may include all the processing and drive amplifiers necessary for driving the spray device 100, in which case, the cable 815 carries power and trajectory signals to the motor(s) and processor(s). Other combinations of electronics locations and wiring are also possible.

Forms of control that the automated actuation system 800 may use to operate the spray device 100 are open-loop control, closed-loop control, or combination thereof. A Proportional, Integration and Differentiation (PID) controller (not shown) may be employed to provide smooth operation of the compression plate assembly 805. Alternatively, a digital controller may be employed. The output from the transducer 335 may be used for closed-loop control of the spray device 100 since the transducer 335 directly measures the effect of the compression plate assembly 805 actuating the spray device 100. Use of open- or closed-loop control may be based on at least one parameter, such as an error budget associated with force, acceleration, velocity, position, length of stroke, or other relevant parameters.

A trajectory input (i.e., an actuation profile) to the compression plate assembly 805 is preferably as close to in vitro actuation of the spray device 100 as possible to test the performance of the spray device 100. In this way, the automated actuation system 800 can actuate the spray device 100 in a manner that allows for near in vitro test conditions. Such testing allows a drug development company or spray device manufacturer to test the performance of the spray device 100. The automated actuation system 800 may be used in conjunction with an automated spray characterization (i.e., spray pattern measurement) system that measures spray pattern, plume geometry, priming and repriming metrics, and/or other metrics associated with actuation of the spray device 100.

FIGS. 9–17 illustrate a processing system and signals captured or generated thereby. The data processing system 900 captures data produced by the transducer 335. The data processing system 900 is typically distinct from control electronics associated with the automated actuation system 800, but data captured, processed, and/or produced by the data processing system 900 may be transferred to the automated actuation system 800 for use in automated actuation of the spray device 100. Data may be transferred between the data processing system 900 and the automated actuation system 800 via a local area network (LAN), magnetic disk, optical disk, infrared signals, a Wide Area Network (WAN) such as the Internet, or other signal or data transfer means.

Figure 9:
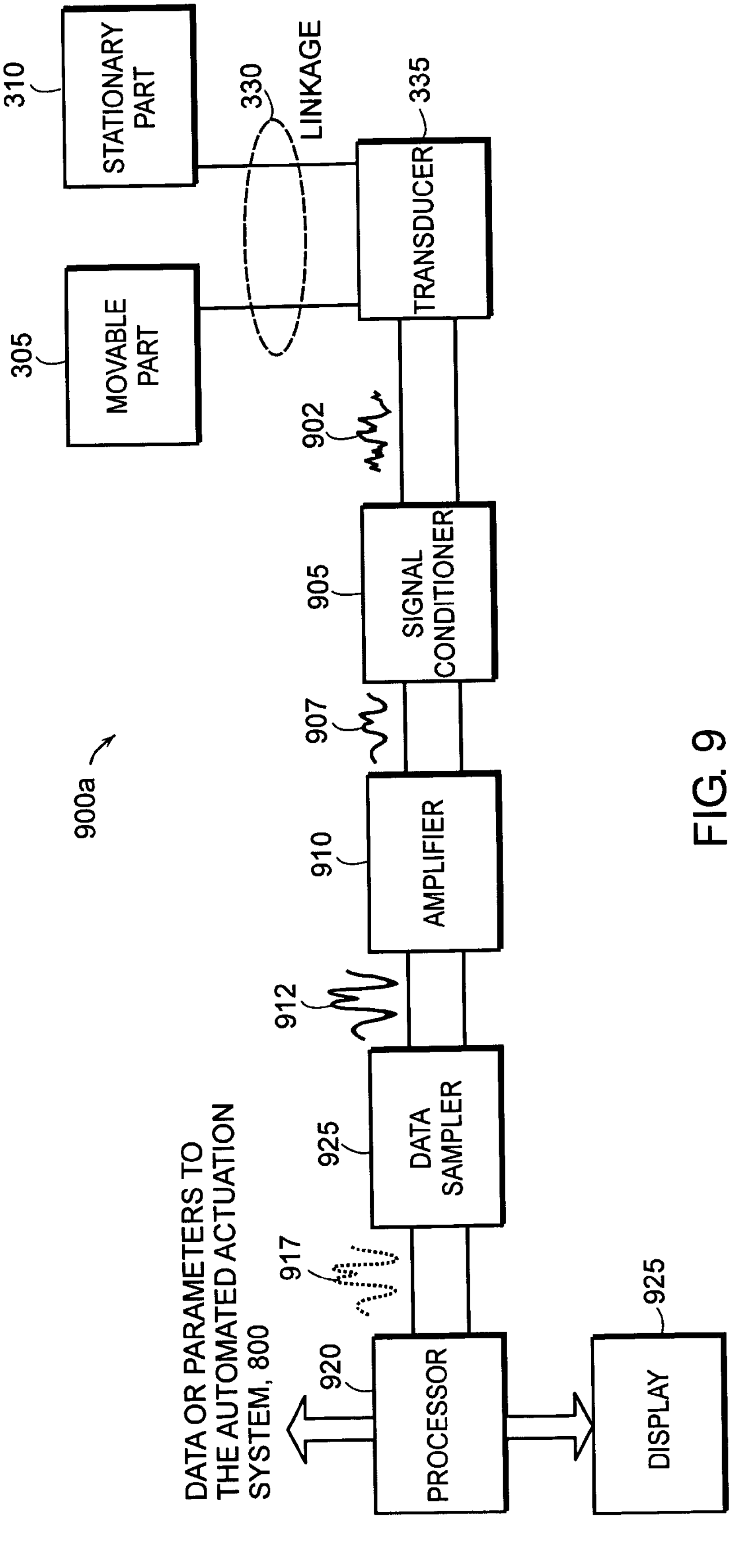
FIG. 9 is a block diagram of a data capture and processing system adapted to be used with the assembly of FIGS. 3 and 4.

Referring first to FIG. 9, the data processing system 900 includes the transducer 335, which receives stimuli via the linkage 330 as a function of the mechanical relationship between the movable part 305 and the stationary part 310. In turn, the transducer 335 indicates the mechanical relationship.

A signal conditioner 905 is connected to the transducer 335 and provides an output signal to an amplifier 910. The amplifier is connected to and provides an output to a data sampler 915. The data sampler 915 is connected to a processor 920. The processor 920 may output information related to the indication of the mechanical relationship between the movable and stationary parts of the spray device 100 on a display 925 and/or transfer data or parameters associated with the data to the automated actuation system 800.

In operation, the signal conditioner 905 provides low-level signal conditioning of signals affected by a change of state of the transducer 335. The signal conditioner 905 may have predetermined knowledge of the type of transducer 335 with which it is in communication. For example, the signal conditioner 905 may provide a consistent current to the transducer 335 if the transducer 335 is a potentiometer. In this example, the signal conditioner 905 may have internal circuitry (not shown) that measures voltage across the potentiometer to provide a measurement as a function of a change of state of the potentiometer caused by a change in length of the linkage 330 resulting from motion of the movable part 305 with respect to the stationary part 310.

The signal conditioner 905 outputs a smooth representation of the voltage to the amplifier 910 corresponding to the indication of the mechanical relationship between the movable and stationary parts of the spray device 100. A waveform 902 represents an example signal indicating motion of the movable part as indicated by the transducer 335. An output from the signal conditioner 905 is shown as a signal 907 that the amplifier 910 amplifies for capture by a data sampler 915. The data sampler, in turn, produces a digitized waveform 917, which is received by the processor 920. The processor 920 may process the digitized signal 917 for determining, for example, parameters associated with in vitro operation of the spray device 100.

Figure 10:
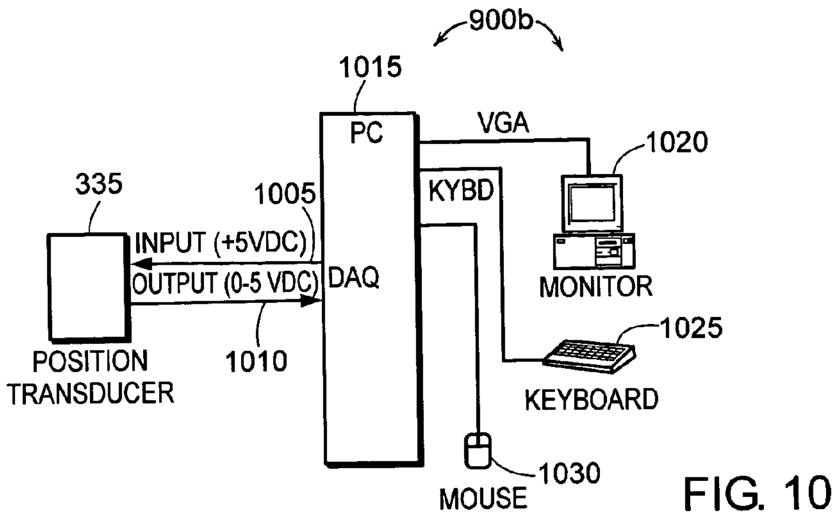
FIG. 10 is an alternative embodiment of the data capture and processing system of FIG. 9.

FIG. 10 is an alternative embodiment of the data processing system 900*b*. The transducer 335 receives an input of +5 VDC 1005 and an output of 0–5 VDC 1010. A data acquisition (DAQ) circuit board 1015 captures the output generated by the transducer 335, which in this case is a position transducer. Therefore, the output from the transducer 335 directly relates to the position of the movable part 305 with respect to the stationary part 310. The DAQ board 1015 may be in communication with a general purpose computer in a daughterboard arrangement. The information captured by the DAQ board 1015 may be displayed on a monitor 1020 and controlled via a Graphical User Interface (GUI) by either a keyboard 1025 or mouse 1030. In this way, a user may provide various parameters and other forms of control to cause the DAQ board 1015 to collect the output 1010 from the transducer 335 in a customized manner.

Figure 11:
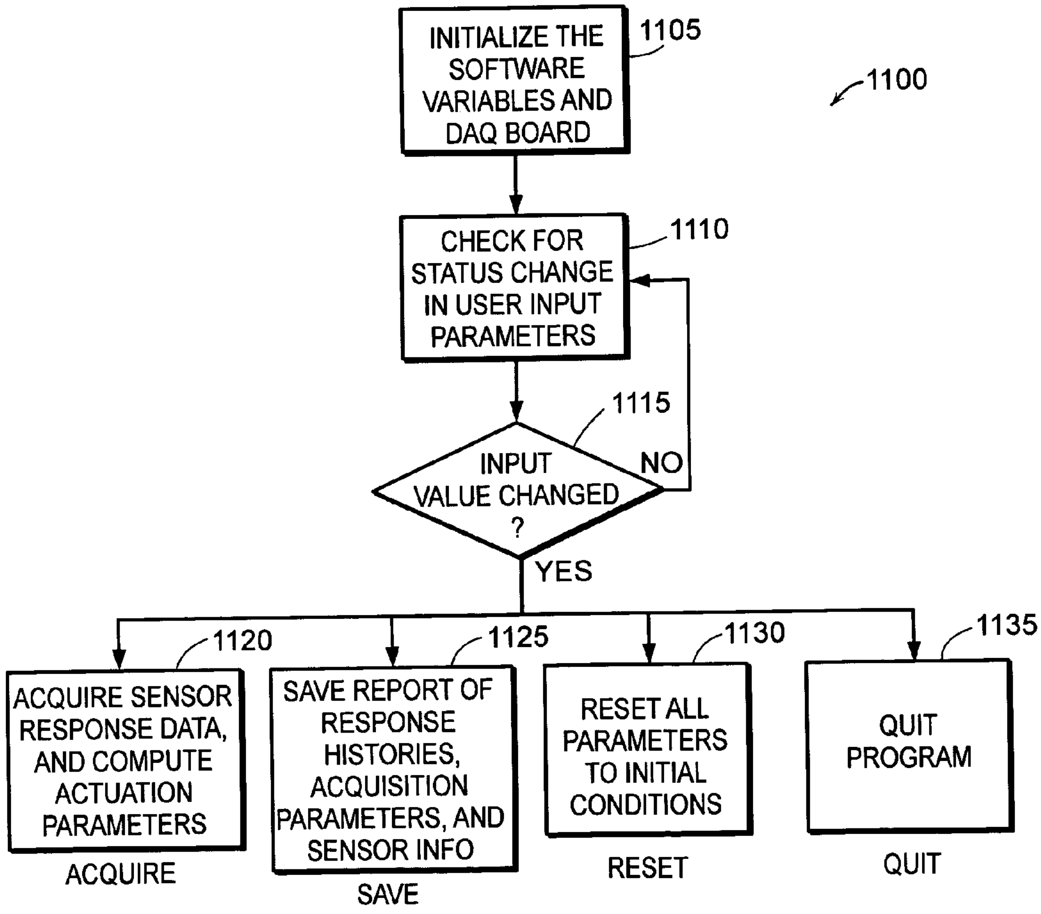
FIG. 11 is a process optionally used with the data capture and processing systems of FIGS. 9 and 10.

FIG. 11 is a flow diagram of a process that may be employed by the data processing systems 900*a*, 900*b*. The process 1100 may start by initializing the software variables in the DAQ board 1015 (step 1105). The process 1100 continues and checks for a status change in user input parameters (step 1110). Examples of user input parameters are sampling frequency, scale factors, and voltage output levels from the DAQ board 1015 to the transducer 335 (i.e., the input 1005 to the transducer 335). If the input value has not changed (step 1115), the process 1100 checks again for a status change in user input parameters (step 1110). If the input value has changed (step 1115), the process 1100 continues to operate as specified by the user.

The process 1100 may acquire sensor response data and compute actuation parameters (step 1120). The process 1100 may also save a report of response histories, acquisition parameters, and sensor information (step 1125). Saving the information may include saving information to a server, local memory, or portable computer readable medium. The process 1100 may also reset all parameters to initial conditions (step 1130). The process 1100 may also quit the program (step 1135) in response to user input. Other processes may also be executed by the process 1100 that are different from the examples listed.

Figure 12:
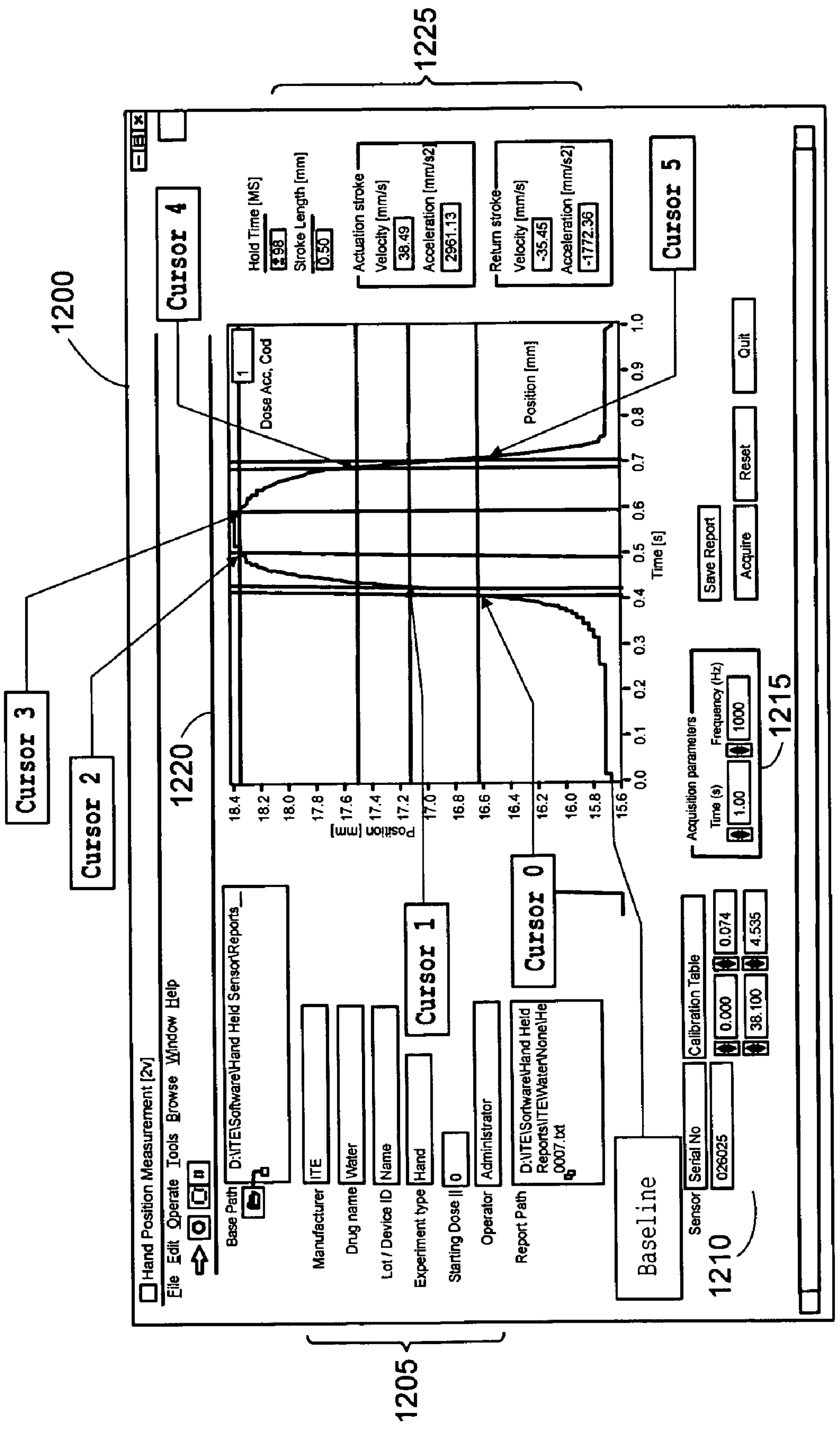
FIG. 12 is a user interface optionally used with the data capture and processing systems of FIGS. 9 and 10.

FIG. 12 is an example Graphical User Interface (GUI) 1200 in which a user may program input conditions, acquisition parameters, and view captured waveforms and associated parameters. A set of input fields 1205 includes information related to materials being tested, and personnel involved in the testing, such as manufacturer, drug name, lot/device ID, experiment type (e.g., hand or automated actuation), starting dose number, operator, and report path to which the captured data is stored. A second set of inputs 1210 relates to the transducer 335, including serial number and a calibration table, where the calibration table allows for input such as gain, dc offset, scale factor, or other parameters related to the calibration of the transducer 335. Another set of parameters input by the use of the GUI 1200 is a set of acquisition parameters, such as data acquisition collection time span (e.g., one second) and sampling frequency (e.g., 1 kHz).

The GUI 1200 also include a graphics area displays a position plot 1220 of the position versus time of the movable part 305 with respect to the stationary part 310. The GUI 1200 displays multiple parameters 1225 associated with the position plot 1220. The parameters 1225 in this embodiment include a hold time of 98 msec, stroke length of 0.50 mm, actuation stroke velocity of 38.49 mm/s, acceleration of 2961.13 mm/$s^2$, return stroke velocity of −35.45 mm/s, and return stroke acceleration of −1772.30 mm/$s^2$. In one embodiment, the measured parameters 1225 are automatically calculated based on the data captured and displayed in the position plot 1220.

Figure 13:
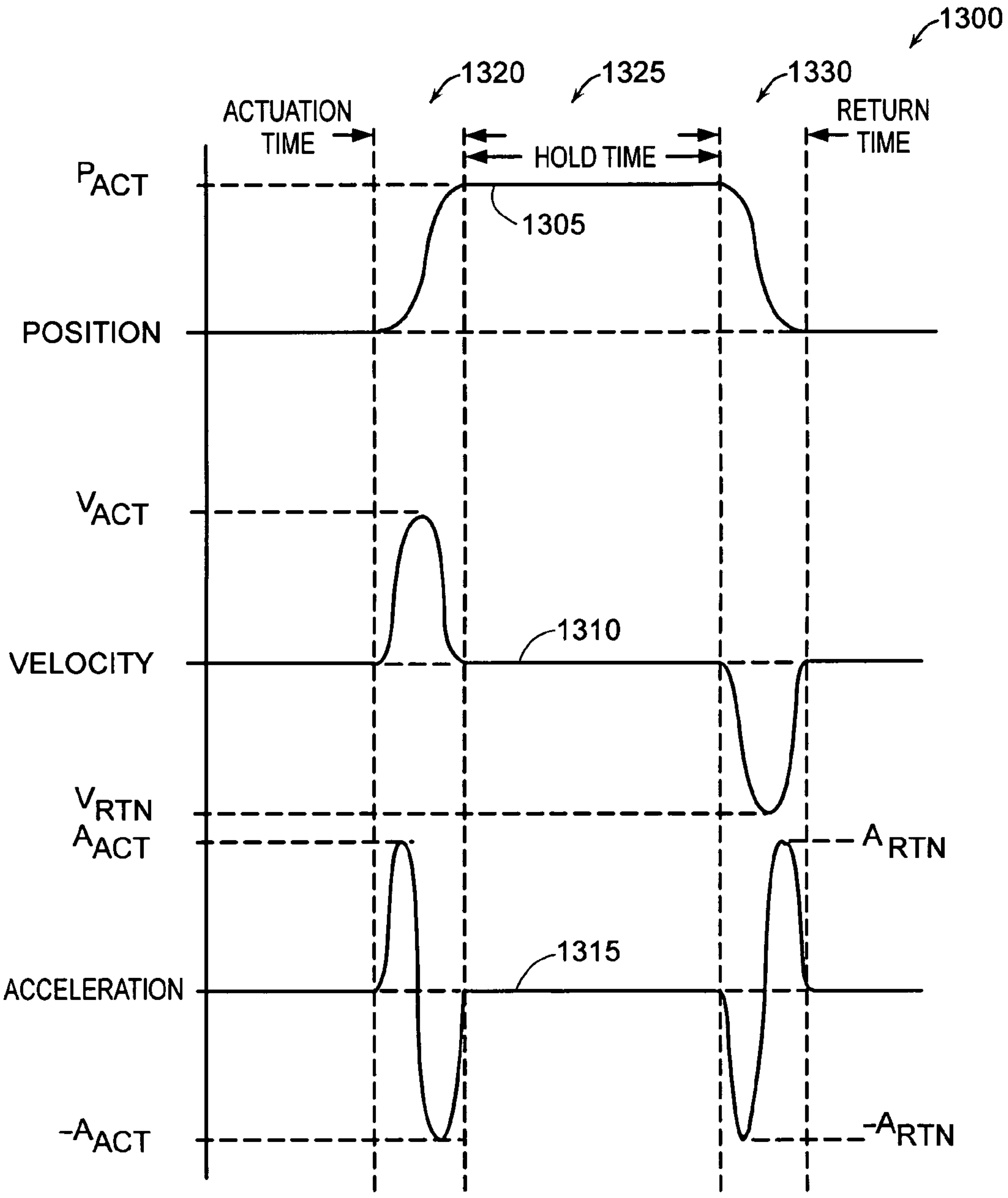
FIG. 13 is a set of waveform diagrams illustrating captured data associated with the spray devices of FIGS. 2A–2B.

FIG. 13 provides graphical representations of position, velocity, and acceleration. The representations are representative of motion of the movable part 305 with respect to the stationary part 310 in a typical spray device 100, 400 by in vitro actuation or automated actuation. A position curve 1305 is similar to the position curve in the position plot 1220 of FIG. 12. The position curve 1305 rises during an actuation time, remains at a position ($P_{ACT}$) during a hold time 1325, and decreases from $P_{ACT}$ during a return time 1330. A corresponding velocity curve 1310 rises to a maximum velocity $V_{ACT}$ halfway during the actuation time and decreases back to a zero velocity during the hold time 1325. The velocity decreases to a maximum negative velocity ($V_{RTN}$) and returns to zero during the return time 1330.

An acceleration curve 1315 illustrates the corresponding acceleration curve 1315 to the position curve 1305 and velocity curve 1310. During the actuation time 1320, the acceleration increases and decreases to maximum accelerations ($A_{ACT}$). Similarly, during the (+/−$A_{ACT}$) return time 1330, the acceleration decreases and increases to maximum accelerations (+/−$A_{RTN}$). The maximum accelerations may be calculated as an average of the magnitude of +/−$A_{ACT}$ levels, and the maximum return accelerations may be calculated as an average of the magnitude of +/−$A_{RTN}$ levels.

Processing to calculate the velocity and acceleration curves from captured position data may be performed in an automated manner. For example, a software routine that calculates velocity or acceleration data from position measurements may use a least squares technique. An example of such a routine may use a Savitzky-Golay smoothing and differentiation filter that optimally fits a set of data points to polynomials of different degrees. This type of filter is useful for substantially reducing noise in a manner better than a point-to-point differentiation technique does. Other smoothing filters and processes may also or alternatively be employed.

It should be understood that if the transducer 335 is an acceleration or velocity transducer, integration and/or differentiation techniques may be used to provide the other motion data, plots, and parameters.

FIGS. 14–17 are plots that were produced by a method to measure hand actuation parameters for nasal spray pumps that can be used for automated actuation. Actuation parameters were measured for representative commercially available spray pumps filled with water. The average actuation parameters were then checked to confirm that the automation actuation system 800 accurately duplicated the ergonomics of hand actuation. The actuation parameters were optimized within a working range of the hand actuation parameters to obtain shot weight delivery closest to the delivery target (e.g., label claim by the pump manufacturer).

Methods for producing the plots of FIGS. 14–17 include a hand actuation portion, a congruency test portion, and an optimized automated actuation portion.

Figure 14:
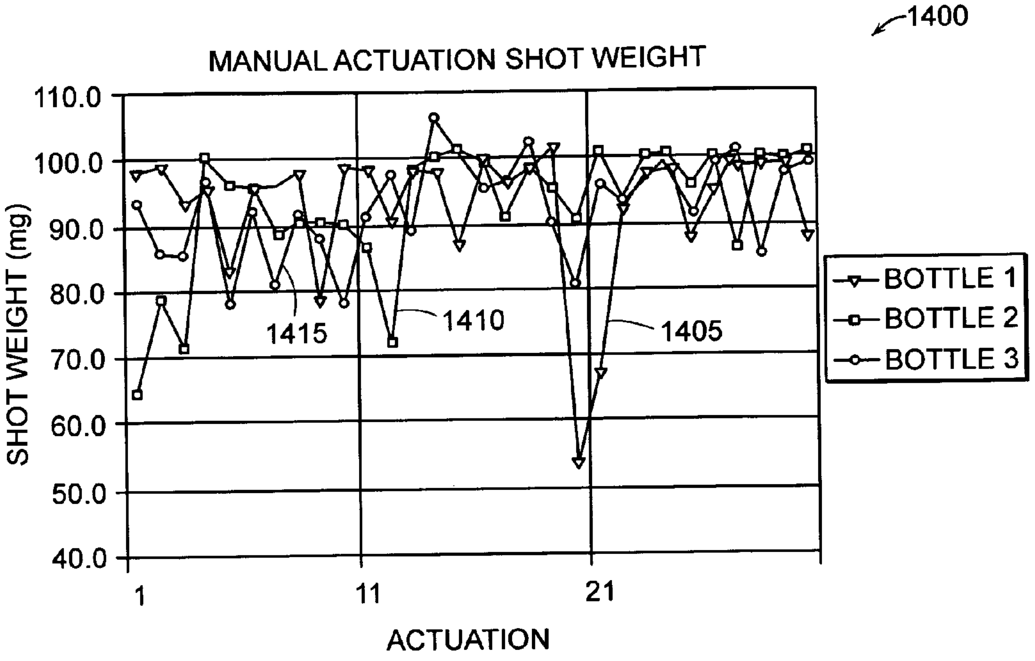
FIGS. 14–17 are actual test data associated with in vitro testing and automated testing of the spray device of FIG. 2A.

Referring first to the hand actuation test portion of the method, three patients were trained on the method for hand actuation. Three primed nasal spray pumps were actuated by hand ten times each by the three patients. The actuation parameters were measured using a data processing system, such as the systems 900*a* and 900*b* of FIGS. 9 and 10, respectively, and the assembly 600 of FIG. 6. After each actuation, expelled shot weight (i.e., liquid expelled during actuation) was measured and is shown in FIG. 14. A curve for each of the three bottles was recorded and displayed in the plot 1400 in FIG. 14.

The shot weight performance by hand actuation of the three nasal spray pumps is shown. The shot weight average was 92.6 mg compared to a design delivery target of 100.2 mg. The standard deviation associated with shot weight was 9.2 mg across all actuations. Bottle 1 (curve 1405) had the highest standard deviation of 10.6 mg across all actuations.

Figure 15:
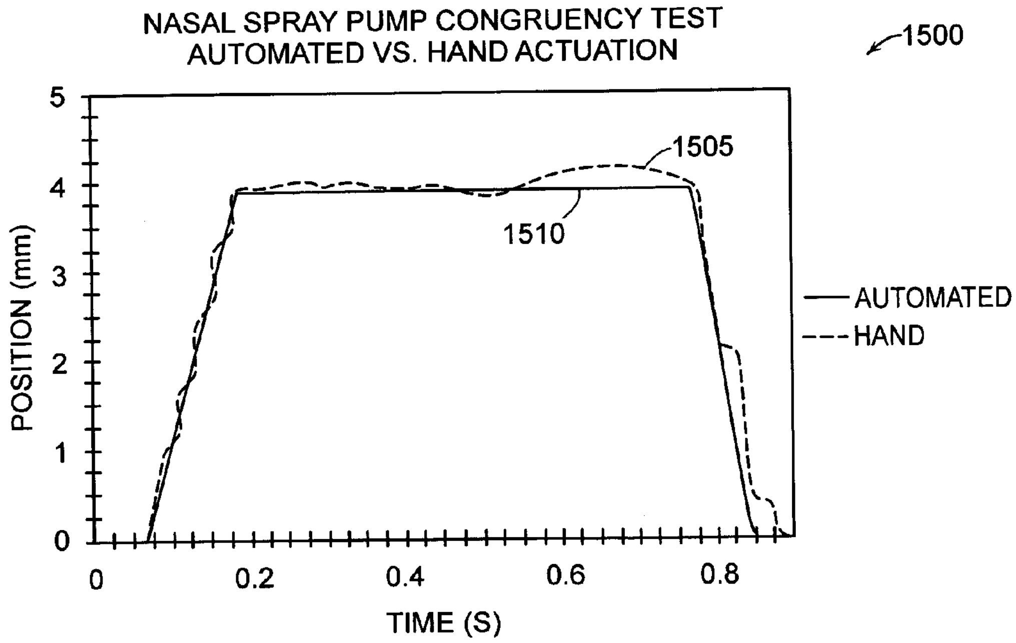
Figure 16:
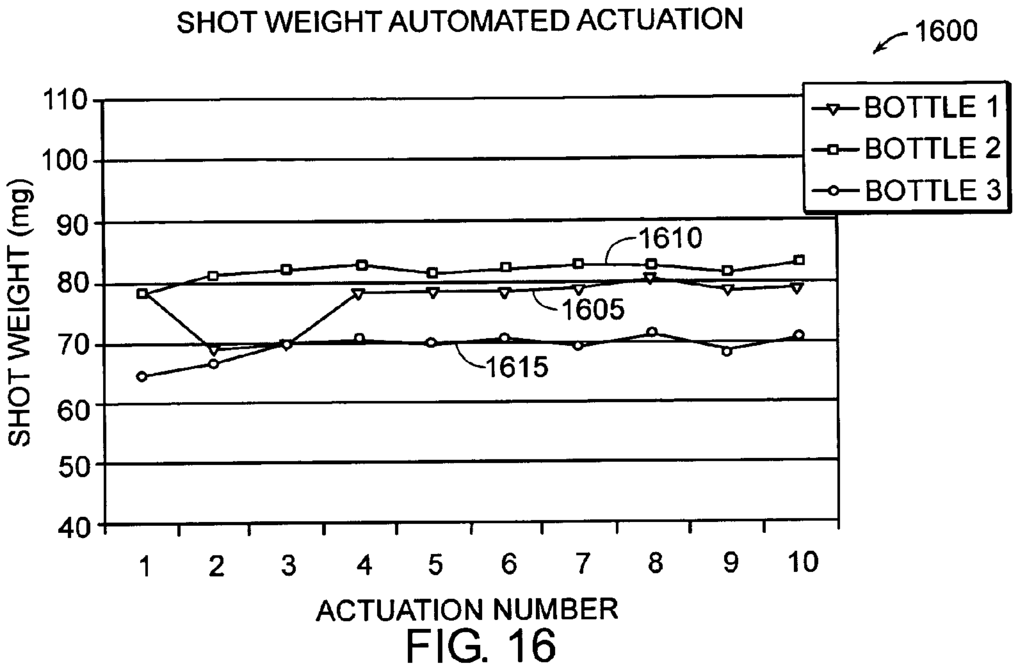

In the congruency test portion of the method, the average actuation parameters from hand actuation were programmed into the automated actuation system 800 of FIG. 8. Three primed spray devices 100 were actuated ten times. A quantitative comparison of the position versus time curves measured by each method is shown in FIG. 15, where the hand measurements are shown in the heavy-lined curve 1505 and the automated measurements are shown in the light-lined curve 1510 in the plot 1500. Shot weight delivery performance for the three units obtained by automated actuation is shown in FIG. 16, with each of the curves 1605, 1610, and 1615 corresponding to spray bottles 1, 2, and 3, respectively, in the plot 1600.

The shot weight performance by automated actuation of three bottles using average actuation parameters (not optimized) is shown. The shot weight average was 76.0 mg. The standard deviation associated with shot weight decreased from 9.2 mg with hand actuation to 5.9 mg across all actuations, using automated actuation, a 35.9% reduction. Bottle 1 (represented by curve 1605) had the highest standard deviation of 4.12 mg across all actuations.

Figure 17:
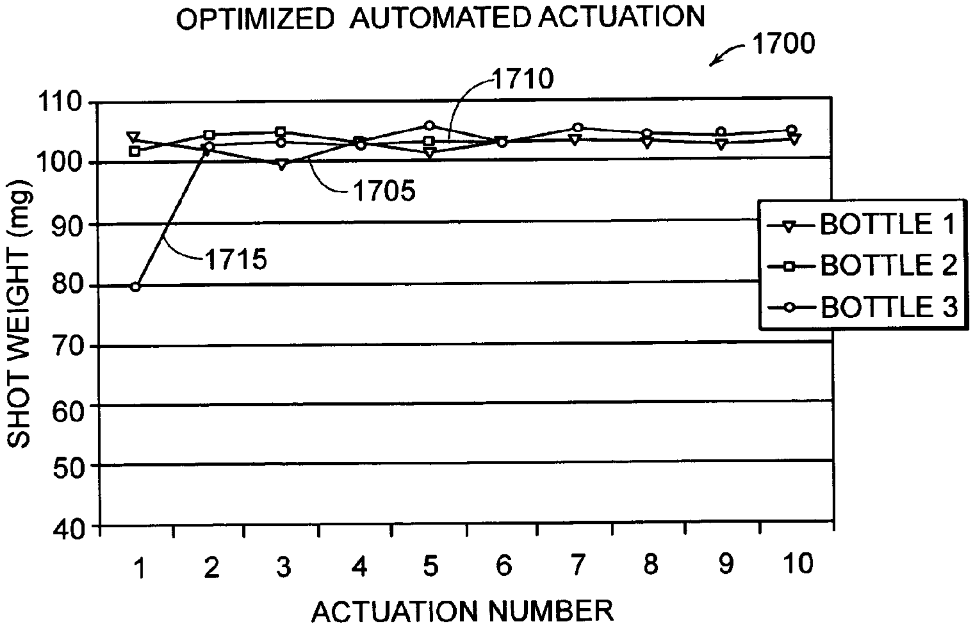

In the optimized automated actuation portion of the method, three primed units were each actuated ten times in a series of tests that independently varied stroke length, hold time, and Intra Actuation Delay (IAD) within the working ranges previously measured during the hand actuation portion of the method. The stroke length was varied from the average value minus one standard deviation ("$-1\sigma$") to the maximum stroke length that did not damage the bottle. The hold time was varied from the average value $-1\sigma$ to the point where the shot weight did not increase more than 10% from previous actuations. The IAD was varied from 30, 15, 5, to 1 second(s). The data were analyzed to find the optimum levels for stroke length, hold time, and IAD, where the optimum was defined as the level which obtained shot weight closest to the nominal specified value (i.e., label claim of the manufacturer). Using the optimum values, three primed units were actuated ten times each to confirm shot weight delivery. A stroke length of 5.11 mm, hold time of 45.55 ms, and IAD of 30 sec provided shot weight delivery performance closest to the nominal specified value (i.e., label claim of the manufacturer) as shown in FIG. 17. Three curves 1705, 1710, and 1715 represent shot weights from bottles 1, 2, and 3, respectively, in the plot 1700.

Shot weight performance using optimized, automated actuation settings was measured. The shot weight average was 101.9 mg compared to a design delivery target of 100.2 mg. The standard deviation associated with shot weight decreased from 9.2 mg with hand actuation to 4.5 mg across all actuations using automated actuations, a 51.5% reduction. Bottle 3 (represented by curve 1715) has the highest standard deviation of 6.19 mg across all actuations.

The results of this process indicates that the automated actuation system 800 (FIG. 8) can be used to accurately measure actuation parameters during hand actuation of three nasal spray pumps. Average hand actuation parameters were programmed into the automated actuation system 800, and the position versus time curves show that the actuator accurately reproduced the ergonomics of hand actuation. Using the automated actuation system 800 reduced the standard deviation associated with shot weight performance from 9.2 mg to 5.9 mg, a 35.9% reduction compared to hand actuation. Within the range of hand actuation parameters, the parameters were varied to optimize the shot weight delivery. The standard deviation associated with shot weight performance was further reduced from 9.2 mg to 4.5 mg, a 51.1% reduction compared to hand actuation. The average shot weight delivery was within 1.7 mg of the target designed delivery value. Determining the actuation parameters may be done prior to conducting any other in vitro measurements, such as spray pattern, plume geometry, or droplet size distribution, to ensure that the automated actuation system 800 consistently simulates hand actuation during these tests.

Figure 18A:
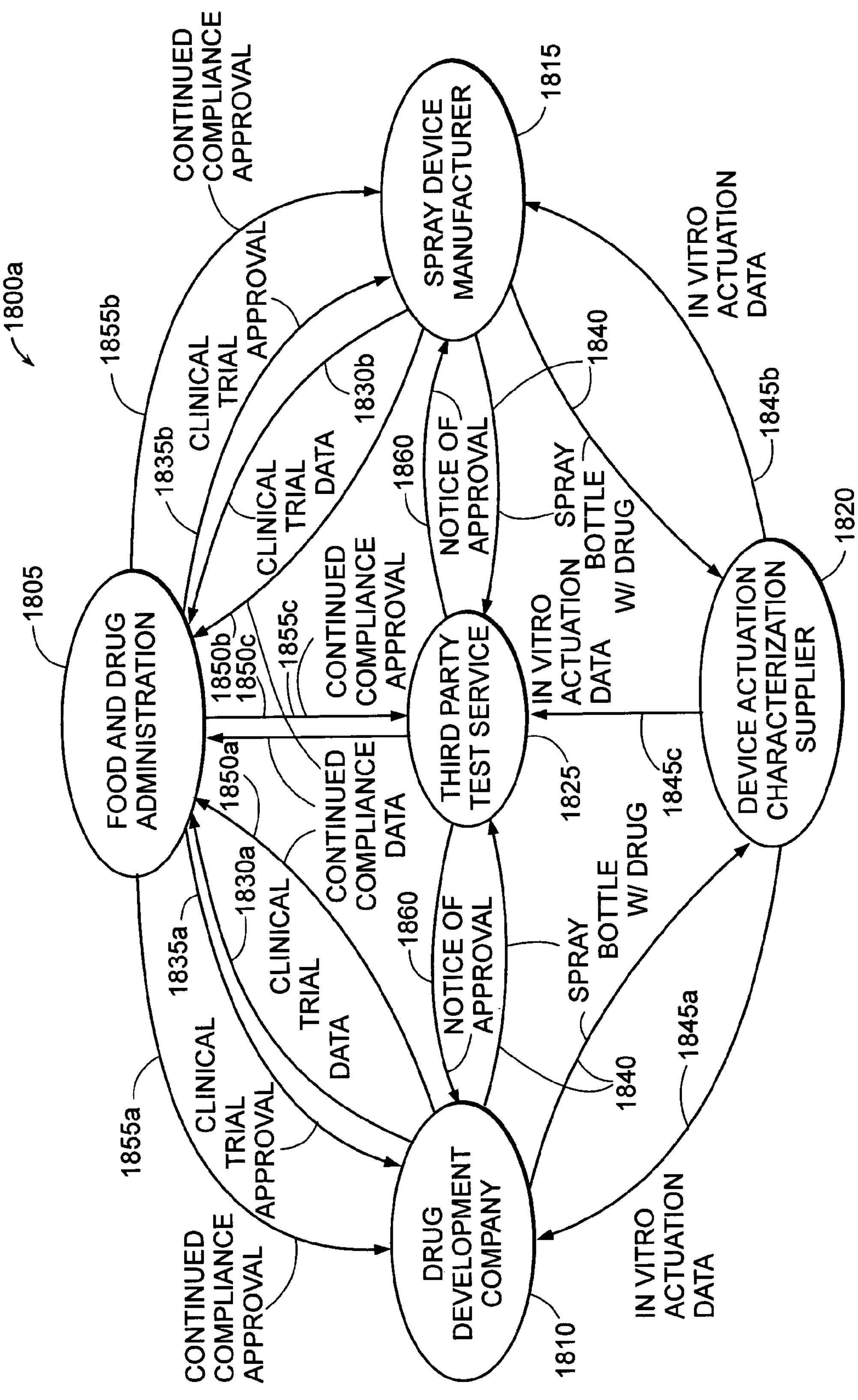
FIG. 18A is a model of a business environment in which another aspect according to the principles of the present invention related to the application of FIG. 1 may be employed.

FIG. 18A is a model 1800*a* of a business environment involving five parties associated with drug and drug delivery development, production, packaging, and distribution. The parties include: (1) the Food and Drug Administration (FDA) 1805, which is a regulatory body, (2) a drug development company 1810, (3) a spray device manufacturer 1815, (4) a device actuation characterization supplier 1820, and (5) a third party test service 1825. This model 1800*a* describes approval cycles for developing a drug, packaging the drug for shipping and in vitro use, obtaining approval in multiple cycles, and characterizing the in vitro performance of spray devices 100, 400 used to deliver the drug, optionally for multiple age groups.

The FDA 1805 is charged with the task of ensuring the drugs are safe for human use. A drug development company 1810 develops a drug and obtains clinical trial data 1830*a*, which is sent to the FDA 1805 for purposes of gaining clinical trial approval 1835*a*. Once the FDA 1805 grants clinical trial approval 1835*a*, the drug development company moves into a production phase of the drug. During the production phase, the drug development company 1810 may use the services of a spray device manufacturer 1815, who may also need to undergo clinical trial approvals.

The spray device manufacturer 1815 manufacturers spray devices 100, 400 and may fill the spray devices 100, 400 with the drug and collect clinical trial data 1830*b* related to production and/or delivery parameters. The clinical trial data 1830*b* may include chemical analysis data and/or metrics, such as spray shot weight, plume geometry, and so forth. The clinical trial data 1830*b* is sent to the FDA 1805. The FDA 1805 reviews the clinical trial data 1830*b* and grants clinical trial approval 1835*b*. Once clinical trial approval 1835*b* is granted, the drug development company 1810 and spray device manufacturer 1815 are approved to produce and distribute the drug in the spray device 100, 400 that was granted clinical trial approval 1835*a*, 1835*b*.

In this cycle of approvals, periodic testing occurs to ensure that what is being manufactured is within the data criteria of the clinical trial approvals 1835*a*, 1835*b*. In other words, the FDA 1805 wants to ensure that distributed drug products fall within the scope of criteria that was deemed to be safe for human use.

In the past, the drug development company 1810 and spray device manufacturer 1815 would perform the tests by hand. The problem with performing the tests by hand is that there is variability in hand actuation of spray devices. Thus, automated actuation of the spray devices 100, 400 is considered to be useful for continued compliance approval to ensure that the drugs and delivery mechanisms adhere to the criteria associated with the clinical trial approvals 1835*a*, 1835*b*.

Not only is automated testing useful for production phases of drug manufacturing and spray device manufacturing, but automated testing may also be used in the clinical trial phases of the drugs. In other words, by using a common automated actuation technique for both the clinical trial phase and production phase approval cycles of a drug and spray device, consistency can be applied to the clinical trial and production phases of the drug development and production cycles, thereby offering the FDA 1805 an increased level of testing consistency and the consuming public an increased level of safety.

Continuing to refer to FIG. 18A, the device actuation characterization supplier 1820 receives spray bottles with drugs 1840, optionally from the drug development company 1810 or spray device manufacturer 1815, depending on the production arrangement between the two companies. For example, the drug development company may purchase spray devices from the spray device manufacturer 1815 and fill a bottle or canister with the drugs. Alternatively, the spray device manufacturer 1815 may purchase the drugs from the drug development company 1810 and fill the spray bottle or canister associated with the spray devices 100, 400 with the drug. A third party manufacturer (not shown) may also be involved and purchase both the drugs and spray devices from each of the companies 1810, 1815 and distribute the drug product. In any case, the device actuation characterization supplier 1820 may characterize the spray bottle with drug 1840 in a manner consistent with the methods and assembly(s) disclosed above in reference to FIGS. 1–17.

The device actuation characterization supplier 1820 collects and distributes in vitro actuation data 1845*a*, 1845*b* to the drug development company 1810 and spray device manufacturer 1815, respectively. The device actuation characterization supplier 1820 may also provide services for in vitro actuation testing, data gathering, and correlating of in vitro hand actuation versus automated actuation of the spray devices to provide useful information for continued compliance testing, and, optionally, initial clinical trial testing.

Using the in vitro actuation data 1845*a*, 1845*b*, the drug development company 1810 and spray device manufacturer 1815 may load and run the data 1845*a*, 1845*b* in automated actuation systems 1800. Optionally, a third party test service 1825 may be employed to run this testing. In any case, the drug development company 1810, spray device manufacturer 1815, or a third party test service 1825 gathers continued compliance data 1850*a*, 1850*b*, and 1850*c*, respectively, which is sent to the FDA 1805 to receive approval for complying with regulations of continuing to ensure that the drugs that are being produced and packaged for use in spray devices 100, 400 are consistent with the original clinical trial approvals 1835*a*, 1835*b*. In turn, the FDA 1805 grants continued compliance approval 1855*a*, 1855*b*, or 1855*c* to each of the companies, respectively. If the third party test service 1825 performs the continued compliance approval testing, then the third party test service 1825 sends a notice of approval 1860 to either the drug development company 1810 or spray device manufacturer 1815, depending on which of the companies hires their services.

It should be understood that the third party test service 1825 may be the device actuation characterization supplier 1820 or a subsidiary of one or both of the drug development company 1810 or spray device manufacturer 1815. Because the lines distinguishing the companies sometimes becomes blurred, it should be understood that a variety of models 1800*a* of business environments can be constructed without departing from the principles of the present invention.

Figure 18B:
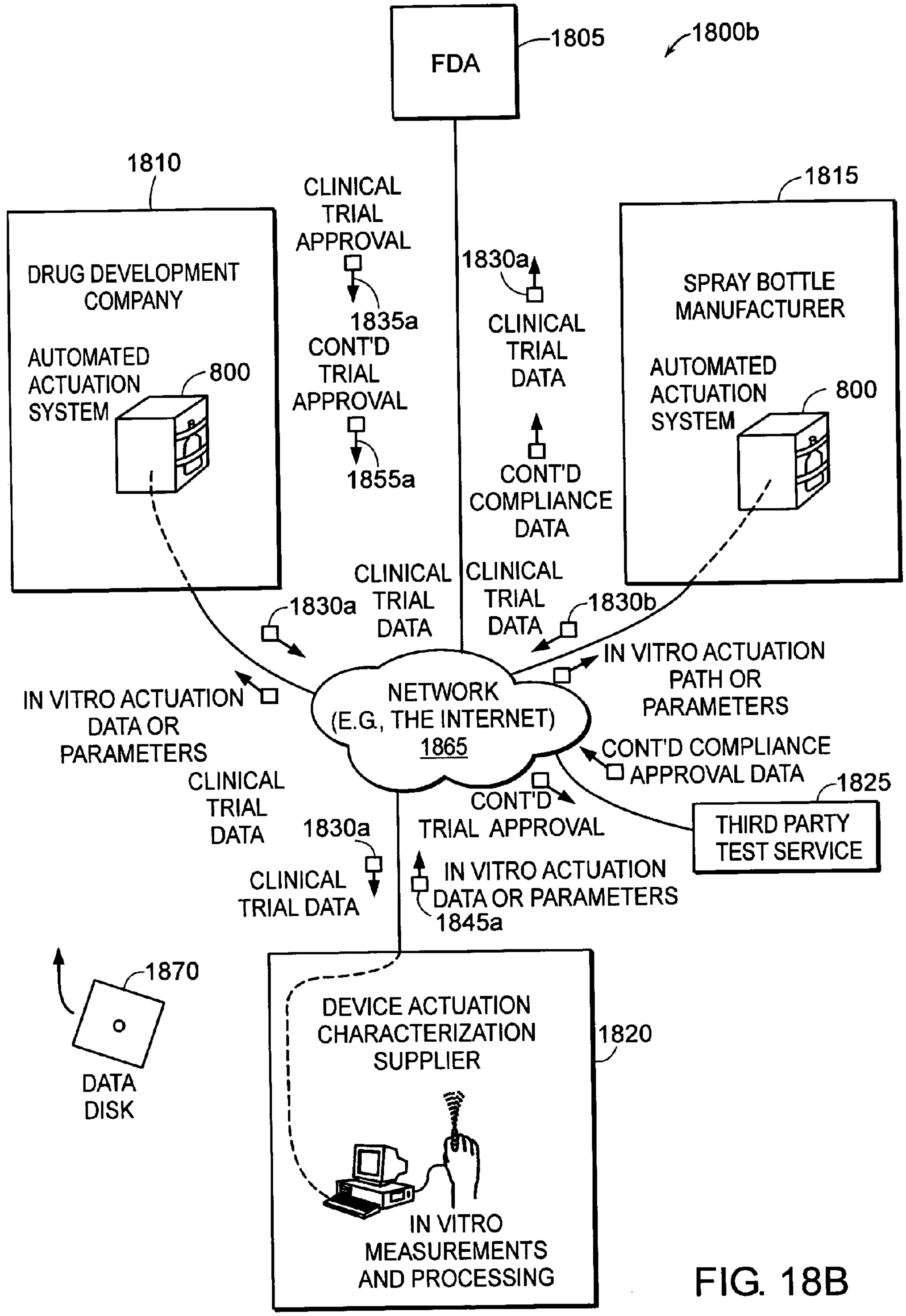
FIG. 18B is a block diagram including the businesses of FIG. 18A communicating via a computer network.

FIG. 18B is a model 1800*b* similar to the model 1800*a* just described. The model 1800*b* includes a computer network 1865, such as the Internet, that is employed to transfer data in data packets, analog or digital modulated signals, or other signaling means to share the data among the parties 1805, 1810, 1815, 1820, and 1825. For example, the in vitro actuation data or parameters 1845*a* may be transmitted from the device actuation characterization supplier 1820 to any of the other parties 1805, 1810, 1815, or 1825 via the network 1865 or through use of a data disk 1870, which may be an optical disk, magnetic disk, or other computer readable media.

Figure 19:
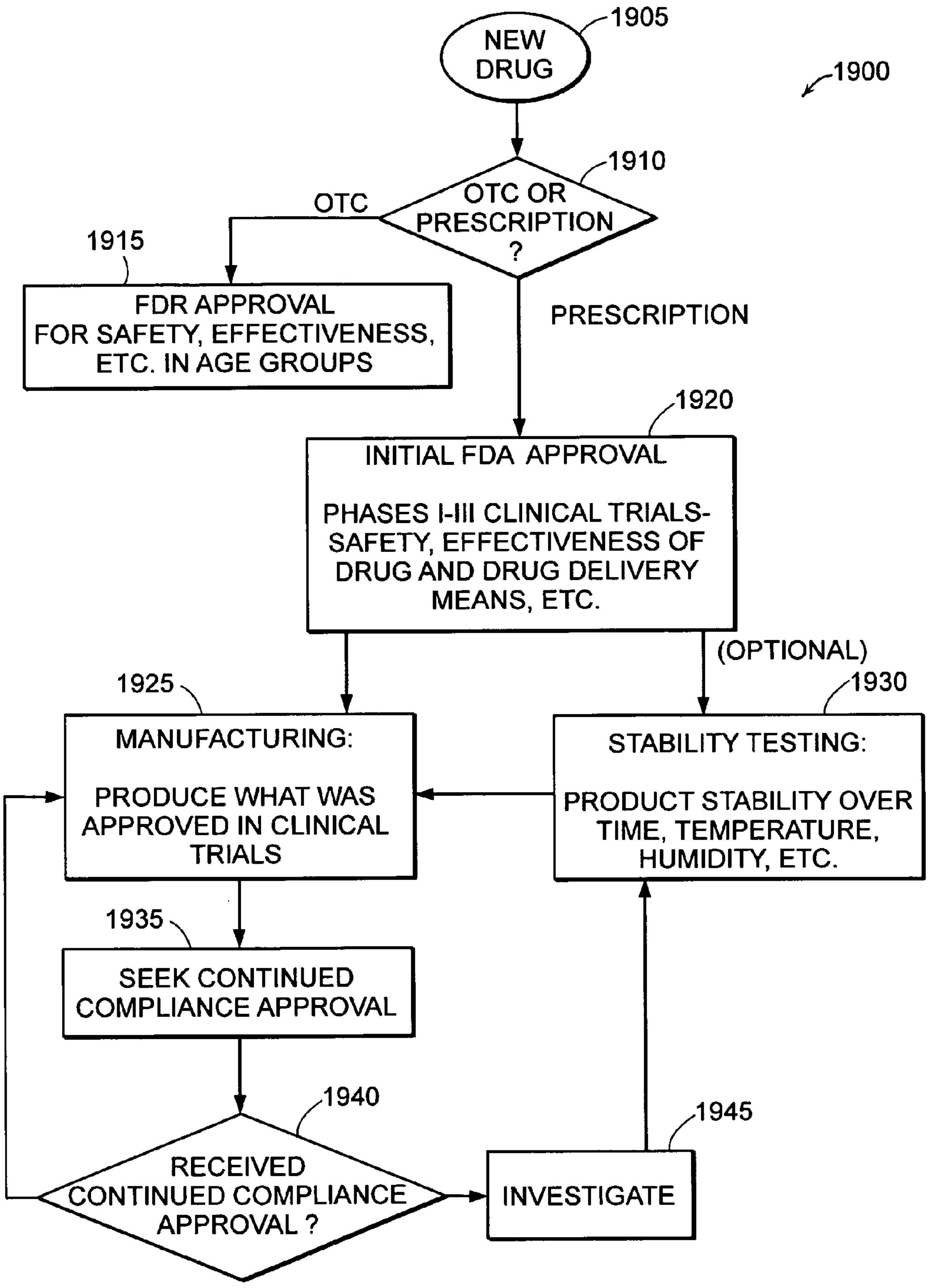
FIG. 19 is a process used in the model of FIG. 18A.

FIG. 19 is a flow diagram or a process 1900 that embodies the approval cycles described above. A process 1900 begins with the drug development company developing a new drug (Step 1905). A determination is made whether the drug is over-the-counter (OTC) or a prescription drug (1910). If the drug is an OTC drug, then the FDA 1805 grants approval based on safety, effectiveness, and so forth in different age groups (Step 1915).

The FDA 1805, in the case of an OTC drug, does not have to grant approval based on the delivery mechanism (i.e., spray device 100, 400). If, however, the drug is a prescription drug (Step 1910), initial FDA approval (Step 1920) must be gained in Phases I–III clinical trials, which test for safety, effectiveness of the drug, drug delivery means, and so forth. An automated actuation system 800 may be useful for the initial FDA approval, described as the clinical trial approvals 1835*a*, 1835*b* in FIGS. 18A and 18B. After gaining initial FDA approval (Step 1920), the drug development company 1810 and spray device manufacturer 1815 begin the manufacturing phase to produce what was approved in the clinical trials (Step 1925). Optionally, the FDA 1805 and/or drug development company 1810 may require further testing, including stability testing (Step 1930), such as product stability over time, temperature, humidity, and so forth.

During the manufacturing cycle, one of the companies 1810, 1815, or 1825 may seek continued FDA approval (Step 1935) to gain continued compliance approval 1855 as described above in reference to FIG. 18A. If the company receives continued compliance approval (Step 1940), the manufacturing of the drug and spray device 100, 400, may be allowed to continue under FDA 1805 auspices; otherwise, an investigation (Step 1945) of the drug and delivery means begins to determine why the data does not show the drug or delivery means meets the criteria associated with the initial clinical trial approval 1835. Therefore, stability testing (Step 1930) or manufacturing (Step 1925) may fall into the investigation cycle. The manufacturing processes (Steps 1925–1945) continue for the lifetime of the drug.

Figure 20:
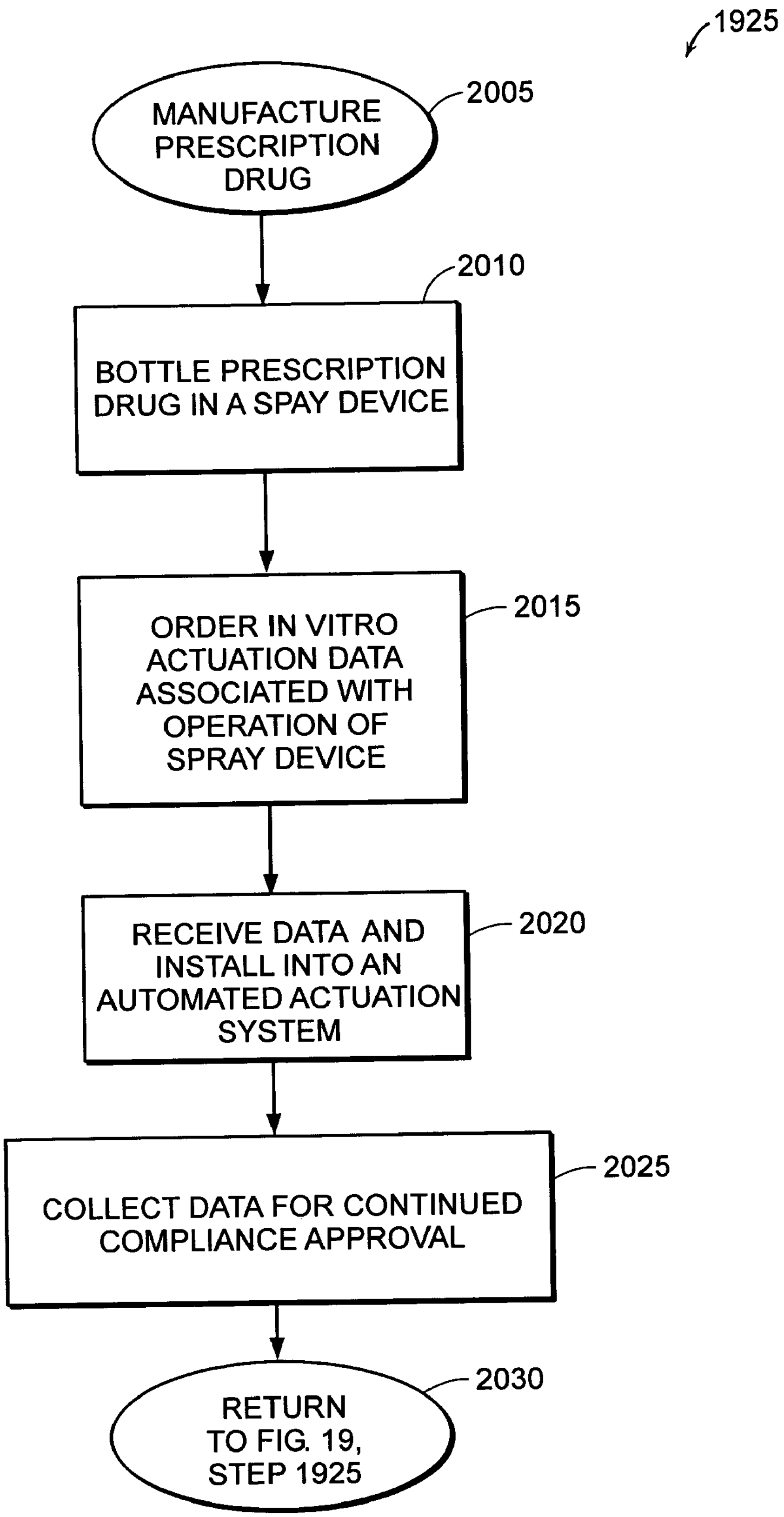
FIG. 20 is a subprocess used in the process of FIG. 19.

An embodiment of a drug manufacturing process (Step 1925) is shown in further detail in FIG. 20. Referring to FIG. 20, the process 1925 begins with the manufacturing of the prescription drug (Step 2005). The drug is bottled in a metered dose spray bottle or canister, or more generically, a spray device 100, 400 (Step 2010). The manufacturer of the drug (e.g., drug development company 1810 or spray device manufacturer 1815) may order the in vitro actuation data associated with operation of the spray device (Step 2015) from the device actuation characterization supplier 1820. The company performing the compliance testing receives the data from the device actuation characterization supplier 1820 and installs the data into an automated actuation system 800 (FIG. 8) (Step 2020). The manufacturing company collects data for continued compliance approval (Step 2025), such as through use of a spray measurement system. The process 1925 returns to the process 1900, Step 1925 of FIG. 19 (Step 2030).

Figure 21:
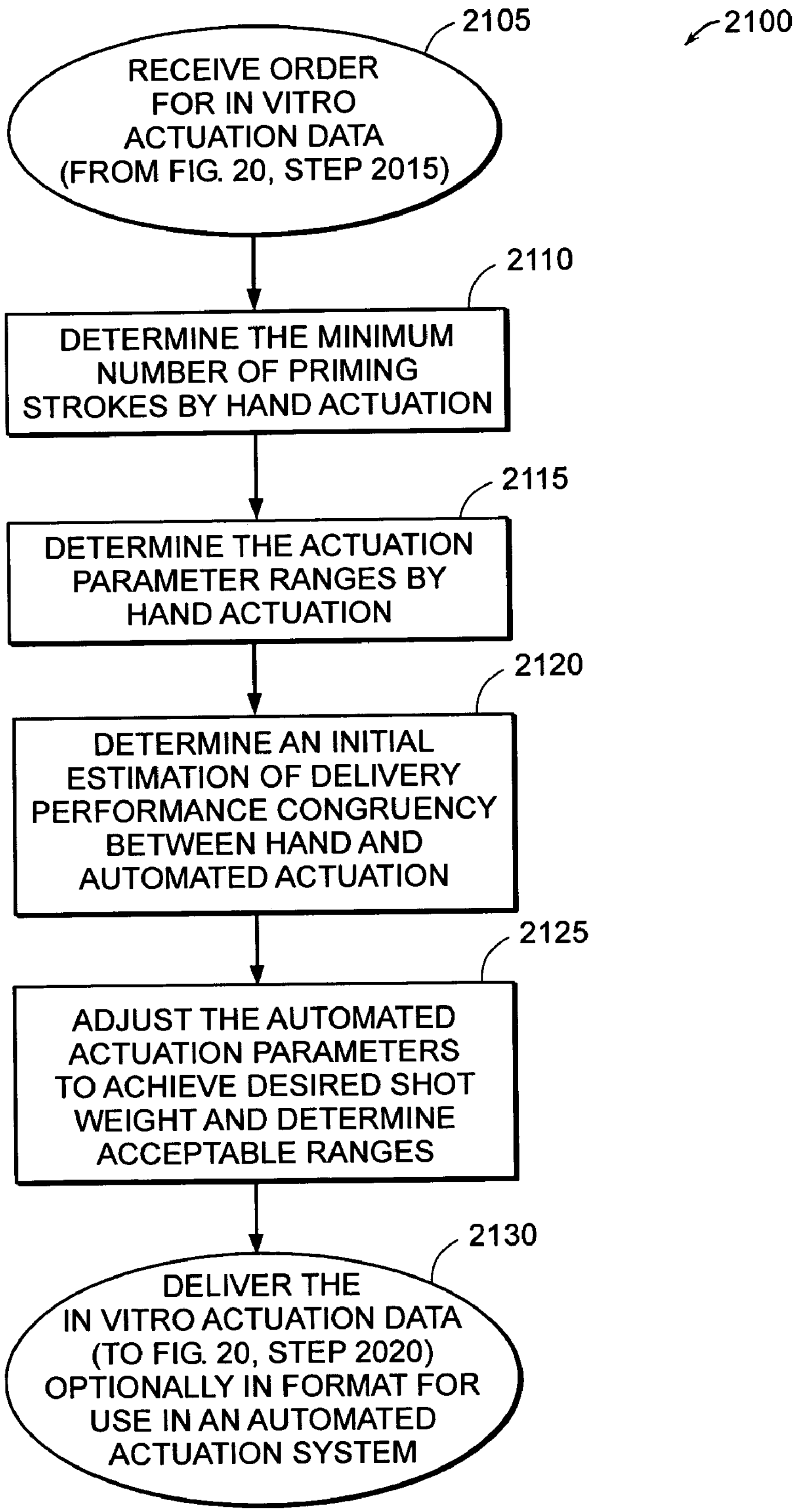
FIG. 21 is a subprocess used in the process of FIG. 20.

Continuing to refer to FIG. 20, the steps associated with ordering in vitro actuation data (Step 2015) and receiving the in vitro actuation data (Step 2020) is further described in FIG. 21.

Referring to FIG. 21, a process 2100 begins with the receipt of the order for the in vitro actuation data from FIG. 20, Step 2015 (Step 2105). The process 2100 continues in which the device actuation characterization supplier 1820 determines a minimum number of priming strokes by hand actuation (Step 2110). The process 2100 continues with a determination of the actuation parameter ranges by hand actuation (Step 2115). A determination of an initial estimation of delivery performance congruency between hand and automated actuation is performed next (Step 2120). The process continues in which an adjustment of the automated actuation parameters to achieve desired shot weight is made, and a determination of acceptable ranges is made (Step 2125). The process 2100 ends (to FIG. 20, Step 2020) with the delivery of the in vitro actuation data, optionally in a format for use in an automated actuation system (Step 2130).

Each of the steps 2110, 2115, 2120, and 2125 is provided in further detail below in steps 1, 2, 3, and 4, respectively.

Step 1. Determine the minimum number of priming strokes by hand actuation.

1.1. Procure the required number of spray pump units filled with drug formulation.

1.2. Select one of the units randomly.

1.3. Measure the weight of the unit on an appropriate balance or scale, and tare the balance with the unit.

1.4. Actuate the unit by hand.

1.5. Record the shot weight data (weight of formulation released during actuation) for each actuation and tare the balance between actuations.

1.6. Repeat steps 1.2–1.5 for the remaining units.

1.7. Analyze the shot weight data from each unit and determine the minimum number of actuations required to obtain stable shot weight performance (e.g., the shot weight being within 95–105% of label claim.)

Step 2. Determine the actuation parameter ranges by hand actuation.

2.1. Procure the required number of spray pump units filled with drug formulation from the same lot(s) used in Step 1, above.

2.2. Select a representative group of people to actuate the units by hand. These people should be trained on how to actuate the units properly, and they should be from a population that corresponds to the age and gender group range for which the product is targeted.

2.3. Have each person actuate each unit by hand a representative number of times and record the position vs. time and shot weight data for each actuation. The position vs. time data may be generated with an appropriate sensor and will be used to determine the settings required by the automated actuation system. The shot weight of each actuation may be measured by an appropriate analytical balance or scale.

2.4. Calculate the minimum, maximum, average, relative standard deviation ("RSD"), and standard deviation ($\sigma$) values for each of the automated actuation system parameters plus shot weight, based on the individual actuation recordings. Additionally, compare the calculated shot weight values to the manufacturer's specifications, if available.

Step 3. Determine an initial estimation of delivery performance congruency between hand and automated actuation.

3.1. Procure the required number of spray pump units filled with drug formulation from the same lot(s) used in Step 1.

3.2. Set the actuation parameters on the automated actuation system to the average values determined in Step 2.

3.3. Prime the units using the minimum number of shots determined in Step 1.

3.4. Actuate each unit with the automated actuation system a representative number of times.

3.5. Record the position vs. time profile and shot weight data for each automated actuation and tare the balance between shots.

3.6. Compile the overall average shot weights and RSD's for the units and compare with those from Step 2.

3.7. Qualitatively compare the position vs. time profiles from hand and automated actuation. Additionally, statistically compare shot weights from hand and automated actuation. If statistical differences appear, investigate the scope and make recommendations as appropriate.

3.8. The definition for delivery performance congruence will be that the measured shot weight values will be within ±1σ of the values specified by the pump manufacturer.

Step 4. Adjust the automated actuation parameters to achieve desired shot weight and determine acceptable ranges.

4.1. Procure the required number of spray pump units filled with drug formulation from the same lot(s) used in Step 1.

4.2. Set the actuation parameters on the automated actuation system to the average values determined in Step 2.

4.3. Prime the units using the minimum number of shots determined in Step 1.

4.4. Automatically actuate each unit a representative number of times using the average parameters determined in Step 2.

4.5. Record the position vs. time profile and shot weight data for each automated actuation and tare the balance between shots.

4.6. Adjust a single actuation parameter (starting with stroke length) in continuous increments of 10% of the average value and repeat Steps 4.4–4.5 until a plateau is reached (10 shot average does not change by more than ±10% of the previous 10 shot average) or until the adjusted actuation parameter is equal to its average value+2σ.

4.7. Compile the overall average shot weights and determine the adjusted actuation parameter range as follows:

Minimum Minimum value to produce shot weight levels within ±1σ of the average from Step 2.

Maximum Maximum value to produce shot weight levels within ±1σ of the average from Step 2, up to the average +2σ.

4.8. Repeat the above steps for the other parameters and compile all of the results.

While this invention has been particularly shown and described with references to preferred embodiments thereof, it will be understood by those skilled in the art that various changes in form and details may be made therein without departing from the scope of the invention encompassed by the appended claims.

For example, the assembly 600 of FIG. 6 illustrates the spray device 100 being held in vertical relationship with a foot assembly 620. However, it should be understood that alternative support techniques may be employed for drug device applications and other applications. For example, the spray device 100 may be held at an angle or horizontally, or even up side down. Further, other embodiments of a shaft 605 and bearing 610 assembly may be employed. For example, the shaft and bearing may be mounted to the spray device 100 as opposed to being in a parallel, off-actuation axis arrangement as shown in FIG. 6. Similarly, the linkage 330 described above as extending through the shaft 605 and locking to the shaft head 615 by way of passing through the central hole 635 through the shaft head 615, may also be clipped onto the bottom of the shaft 605 closest to the transducer 335.

The motor(s) that drive the compression plate assembly 805 in FIG. 8 may be external from the guide bars 810 or drive rod 830, as described above, or integral with the guide bars 810 or drive rod 830. For example, one or more of the guide bars 810 or drive rod 830 may be a threaded screw and be driven by a motor in a worm-gear arrangement with the compression plate assembly 805, which has a complementary thread in such an embodiment. Another example includes a slot in the guide bars 810 or drive rod 830 with a drive mechanism located inside that is connected to a mating assembly on the compression plate assembly 805. Further, the automated actuation system 800 may include a mechanism that connects to the mounting assembly 320*c* in a manner adapted to actuate the spray device 100 absent the compression plate assembly 805.

Also, although electrical components (e.g., potentiometer) for measuring displacement or motion of the adapter assembly 315 with regard to the mounting assembly 320 is described herein, other embodiments of transducers may be employed, such as optical sensors (e.g., interferometers) or non-contact electrical sensors, such as hall effect sensors or capacitive probe sensors, where the sensors function in a manner essentially equivalent to a transducer 335. Similarly, although a transducer cable 340 is illustrated in the embodiment of FIG. 6, it should be understood that infrared or Radio Frequency (RF) means for transmitting transducer data indicating position or motion between the adapter assembly 315 and mounting assembly 320 may be employed.

With regard to the data collection and processing system of FIG. 9, alternative embodiments may be employed. For example, the system 900*a* may not use a signal conditioner 905; instead, the system 900*a* may use an amplifier 910 that provides minimal noise or has a signal conditioner 905 integral in the amplifier 910. Also, various forms of data samplers 915 may be employed. For example, a traditional 12- or 16-bit data sampler 915 may be employed. It should be understood that other data samplers, including non-traditional data samplers may also be used.

The transducer 335 may have a draw wire with a stroke length/displacement range of 0–1.5 inches. The electrical output circuitry for the transducer 335 may form a simple voltage divider with the output voltage signal scaling linearly with the absolute position of the draw wire. In addition, the DAQ board 1015 may have a 5 volt DC output that can be used as the input voltage for the transducer 335, and this sets the output range of the sensor to be 0–5 volts DC, corresponding to 0–1.5 inches of displacement, respectively. In addition, this output range is preferably compatible with the input measurement range of the DAQ board 1015. This DAQ board 1015 may be able to read and record the analog voltage signal 902 from the transducer 335 up 10 kHz or more. In addition, the DAQ board 1015 may be designed to operate in a standard personal computer.

A portable or desktop computer system is typically suitable for use with the present invention. The computer system preferably works with the DAQ board 1015 and associated control software.

The processor 920 may be a general purpose processor or a specialized signal processor. Similarly, the data acquisition board 1015 of FIG. 10 may be a specialized data acquisition board operating in a computer or a microprocessor adapted to work within the environment to receive analog or digital information from the transducer 335. For example, the transducer may be a digital encoder or resolver and provide the information directly as a digital word or data stream.

The graphical user interface 1200 of FIG. 12 may be a text based interface or other form of interface, such as a touch screen. The user may be allowed to select various points along the curve(s) alone or in combination with automated data capture and processing techniques, which include selection of various parameters associated with position, velocity, or acceleration.

Control software associated with the present invention may be designed to perform the following functions: (i) record the position vs. time history of the compression and return stroke trajectories; (ii) verify the proper operation of the transducer 335 and DAQ board 1015; and (iii) automatically determine the stroke length of the spray device 100, 400, the velocity and acceleration achieved during the compression and return strokes, and the hold time of the stroke (the time spent at the fully compressed position).

The curves of FIGS. 14–17 are indicated for three users. However, it should be understood that many more users of the spray device 100, 400 may be involved in the testing to make more accurate measurements and determine accurate parameters. Further, persons of multiple age groups, sizes, hand sizes, health, hand impairments (e.g., carpal tunnel syndrome), and other criteria may be used in the testing and actuation characterization process.

Image Therm Engineering, Inc.'s (Sudbury, Mass.) Spray-VIEW NSx, MDx, and OSx automated actuation systems are examples of automated actuation systems 800 of FIG. 8 suitable for use with the present invention. These systems allow programming of stroke length, compression and return stroke velocity and acceleration, and hold time levels. The output from the processor 920 may be used directly as inputs to these systems, thus allowing a simple transition from the required exploratory studies to automated actuation to be achieved and documented. In addition, the assembly 600 could be used simultaneously with these automated systems to verify their proper operation.

It should also be understood that the FDA 1805 is an example of a regulatory body. Alternatively, depending on the application, the regulatory body may be a different department of the U.S. or foreign government, such as the Department of Defense (DOD), National Institute of Health (NIH), or a non-governmental body, such as a regulatory body that defines paint colors, for example. Moreover, the regulatory body may not necessarily "regulate" an industry, but, instead, "suggest" or recommend certain industry-wide parameters. For purposes of this application, the regulatory body definition covers government and non-government regulatory bodies as well as non-regulatory bodies per se.

The computer network 1865 of FIG. 18B may be other forms of computer networks based on different arrangements of the companies 1810, 1815, 1820, or 1825, depending on organization of these companies, such as if the companies are subsidiaries, sister companies, and so forth.

The processes of FIGS. 19–21 may be different for the drug and drug delivery industries based on changing rules, regulations, and guidelines defined by the regulatory body (e.g., FDA 1805) governing the industry. However, it should be understood that if a different regulatory body is involved with this or other processes associated with the clinical trial and continued approval process cycles described herein, the process or steps may vary without departing from the principles of the present invention. Moreover, in different industries, the processes may be industry dependent and vary accordingly.

It should be understood that any of the data collecting or processing may be implemented in hardware, firmware, or software. If implemented in software, instructions may be stored on computer-readable media, such as magnetic disk, optical disk, read only memory (ROM), random access memory (RAM), loaded on a server and transmitted across a computer network, or stored on any other form of computer readable medium. A processor loads the software instructions from the computer-readable medium and executes the instructions to perform the processes described herein.

The assembly 600 may be used to record the position vs. time trajectories achieved during actuation of pharmaceutical spray pump assemblies and also for other applications. Examples of other applications include the following: characterization of glue/caulking guns, household spray pumps, pressurized spray cans, and pharmaceutical nasal syringes; testing of robotic actuation of industrial nozzles; and/or actuation of cosmetic spray pumps.

What is claimed is:

1. A method of servicing companies associated with a spray device operating under guidelines of a regulatory body, the method comprising:

capturing in vitro actuation data associated with operation of a spray device; and distributing the data to a company associated with an aspect of the spray device for testing the spray device to ensure continued compliance with prior approval of the spray device by a regulatory body.

2. The method according to claim 1 further including converting the data to parameters and distributing the data in the form of the parameters.

3. The method according to claim 1 wherein the spray device includes a stationary part and a movable part, and wherein the data includes a mechanical relationship between the stationary part and the movable part versus time.

4. The method according to claim 3 further including measuring position, velocity, or acceleration relationships between the stationary part and the movable part.

5. The method according to claim 1 wherein capturing the in vitro actuation data includes sorting the data based on in vitro age groups.

6. The method according to claim 1 wherein capturing the in vitro actuation data includes determining a minimum number of priming strokes by hand actuation.

7. The method according to claim 1 wherein capturing the in vitro actuation data includes determining actuation parameter ranges by hand actuation.

8. The method according to claim 1 wherein capturing the in vitro actuation data includes determining an initial estimation of delivery performance congruency between hand and automated actuation.

9. The method according to claim 8 further including adjusting automated actuation parameters associated with the automated actuation to achieve a desired shot weight and to determine acceptable ranges.

10. The method according to claim 1 wherein distributing the data includes providing the data in a format executable by a machine configured to actuate the spray device in an automated manner.

11. The method according to claim 1 wherein the prior approval is a clinical trial approval.

12. The method according to claim 1 wherein the company is a drug development company.

13. The method according to claim 1 wherein the company is a spray device manufacturer.

14. The method according to claim 1 wherein the company is a testing service provider.

15. The method according to claim 1 wherein the regulatory body is the Food and Drug Administration (FDA).

* * * * *

UNITED STATES PATENT AND TRADEMARK OFFICE

CERTIFICATE OF CORRECTION

PATENT NO. : 7,100,839 B2 
APPLICATION NO. : 10/824778
DATED : September 5, 2006
INVENTOR(S) : Dina J. Farina et al.

It is certified that error appears in the above-identified patent and that said Letters Patent is hereby corrected as shown below:

On The Title Page, item (57)
Under inventors, please change the spelling of inventor “Franklin A. Bales” to --Franklin E. Bales--.

Signed and Sealed this

Twenty-third Day of January, 2007

JON W. DUDAS
*Director of the United States Patent and Trademark Office*